United States Patent
Beauglehole et al.

(10) Patent No.: US 7,985,754 B2
(45) Date of Patent: Jul. 26, 2011

(54) SELECTIVE ANTAGONISTS OF $A_{2A}$ ADENOSINE RECEPTORS

(75) Inventors: Anthony Beauglehole, Charlottesville, VA (US); Jayson M. Rieger, Charlottesville, VA (US); Robert D. Thompson, Charlottesville, VA (US)

(73) Assignee: Trovis Pharmaceuticals, LLC, Newton, MA (US)

( * ) Notice: Subject to any disclaimer, the term of this patent is extended or adjusted under 35 U.S.C. 154(b) by 889 days.

(21) Appl. No.: 11/879,133

(22) Filed: Jul. 16, 2007

(65) Prior Publication Data

US 2009/0118309 A1    May 7, 2009

Related U.S. Application Data

(60) Provisional application No. 60/807,545, filed on Jul. 17, 2006.

(51) Int. Cl.
    C07D 473/34    (2006.01)
    A61K 31/52     (2006.01)
    A61P 35/00     (2006.01)
    A61P 25/16     (2006.01)
    A61P 25/14     (2006.01)

(52) U.S. Cl. ................ 514/263.22; 514/263.4; 544/277

(58) Field of Classification Search ............... 544/277; 514/263.22, 263.4
    See application file for complete search history.

(56) References Cited

U.S. PATENT DOCUMENTS

| | | |
|---|---|---|
| 2007/0270373 A1 | 11/2007 | Rieger et al. |
| 2008/0009460 A1 | 1/2008 | Linden et al. |
| 2008/0027022 A1 | 1/2008 | Linden et al. |
| 2008/0262001 A1* | 10/2008 | Kranenburg et al. .... 514/263.22 |
| 2008/0312160 A1* | 12/2008 | Guerrant et al. ................ 514/19 |
| 2009/0181920 A1* | 7/2009 | Watkins et al. ................ 514/45 |
| 2009/0280059 A1* | 11/2009 | Rieger et al. ............... 536/27.22 |

* cited by examiner

*Primary Examiner* — Mark L Berch
(74) *Attorney, Agent, or Firm* — McCarter & English, LLP

(57) ABSTRACT

The present invention provides compounds of formulae Ia and Ib:

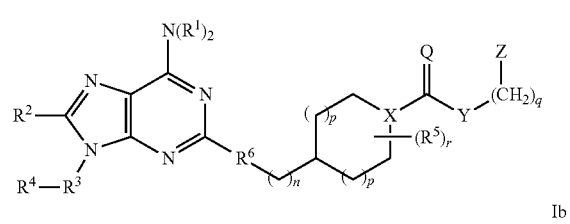

wherein $R^{1-5}$, Q, X, Y, Z, p, q, and r are as defined herein. The compounds are potent and selective antagonists of $A_{2A}$ adenosine receptors (ARs). The invention further includes pharmaceutical compositions containing these compounds and methods of using the same.

19 Claims, No Drawings

SELECTIVE ANTAGONISTS OF A$_{2A}$ ADENOSINE RECEPTORS

This application claims the benefit of U.S. Provisional Application No. 60/807,545, filed Jul. 17, 2006, the disclosure of which is incorporated herein in its entirety.

FIELD OF THE INVENTION

The present invention relates to compounds and pharmaceutical compositions that are selective antagonists of the A$_{2A}$ adenosine receptor (AR). These compounds are useful as pharmaceutical agents.

BACKGROUND OF THE INVENTION

Selective antagonists of A$_{2A}$ adenosine receptors have proven to be effective for the treatment of Parkinson's disease (PD) both in animal models and in a human trial. (See Hauser et al, *Neurology* 2003, 61, 297-303). The first relatively selective A$_{2A}$AR antagonists were the 8-styrylxanthines, for example KW-6002, which has low nanomolar affinity for the A$_{2A}$AR and >100-fold selectivity for the A$_{2A}$AR over the A$_1$AR. KW-6002, entered clinical trials in 2002 as an agent for the treatment of PD. (See Bara-Jimenez et al, *Neurology* 2003, 61, 293-296) SCH58261, a pyrazolo[4,3-e]-1,2,4 triazolo[1,5-c]pyrimidine was a prototype for a series of second-generation derivatives that also have low nanomolar affinity and good selectivity for the A$_{2A}$AR in vitro. (See Zocchi et al, *Br. J. Pharmacol.* 1996, 117, 1381-1386.) The third class of antagonists to appear, the 1,2,4-triazolo[4,5-e]-1,3,5-triazines, was typified by ZM241385, which is active at the A$_{2A}$AR in the sub-nanomolar range but had some cross reactivity. (See Keddie et al, *Eur. J. Pharmacol.* 1996, 301, 107-113.)

These potent A$_{2A}$ antagonists have been important research tools, greatly facilitating pharmacological investigations of A$_{2A}$AR function in vitro as well as in vivo and significantly enhancing our understanding of the neurobiology of the A$_{2A}$AR. However, each of these antagonists has important drawbacks. KW-6002 is light-sensitive and undergoes photoisomerization from the active E-isomer to the 800-fold less active Z-isomer. SCH58261 is very poorly soluble and even its second-generation derivatives have marginal bioavailability. ZM241385 not only is modestly selective but also has poor bioavailability. Other nitrogen heterocycles, such as the 1,2,4-triazolo[4,3-a]quinoxalin-1-ones and the oxazolo[4,5-d]pyrimidines from ICI, are also unselective, and their bioavailability is unknown. (See Colotta et al, *Arch. Pharm.* (*Weinheim*) 1999, 332, 39-41.)

Although adenosine receptor subtype-selective probes are available for the A$_1$, A$_{2A}$, A$_{2B}$, and A$_3$ ARs, few selective antagonists with acceptable in vitro and in vivo properties are available. Therefore, a continuing need exists for compounds that are selective A$_{2A}$ receptor antagonists.

SUMMARY OF THE INVENTION

The present invention provides compounds that act as antagonists of A$_{2A}$ adenosine receptors and stereoisomers and pharmaceutically acceptable salts thereof.

The invention also provides pharmaceutical compositions comprising a compound of the present invention or stereoisomer or a pharmaceutically acceptable salt thereof in combination with a pharmaceutically acceptable carrier.

Additionally, the invention provides a therapeutic method for treating a pathological condition or symptom in a mammal, such as a human, wherein the activity, e.g., over-activity, of adenosine A$_{2A}$ receptors is implicated in one or more symptoms of the pathology and antagonism (i.e., blocking) of their activity is desired to ameliorate said symptoms. Thus, the present invention provides a method of treating a disease comprising administering a therapeutically effective amount of at least one compound of the present invention or a stereoisomer or pharmaceutically acceptable salt thereof, wherein the disease is selected from movement disorders, cancer, addictive disorders (e.g., smoking, alcohol, drugs).

The invention provides a compound of the present invention for use in medical therapy.

The invention also provides the use of a compound of the present invention for the manufacture of a medicament.

Other objects, features and advantages of the present invention will become apparent from the following detailed description. It should be understood, however, that the detailed description and the specific examples, while indicating aspects of the invention, are given by way of illustration only, since various changes and modifications within the spirit and scope of the invention will become apparent to those skilled in the art from this detailed description.

DETAILED DESCRIPTION OF THE INVENTION

Applicants have discovered that compounds of the present invention can be useful for the treatment of diseases associated with deleterious A$_{2A}$ receptor activation or activity.

In an aspect, the present invention provides novel compounds of formula Ia or Ib or stereoisomer or a pharmaceutically

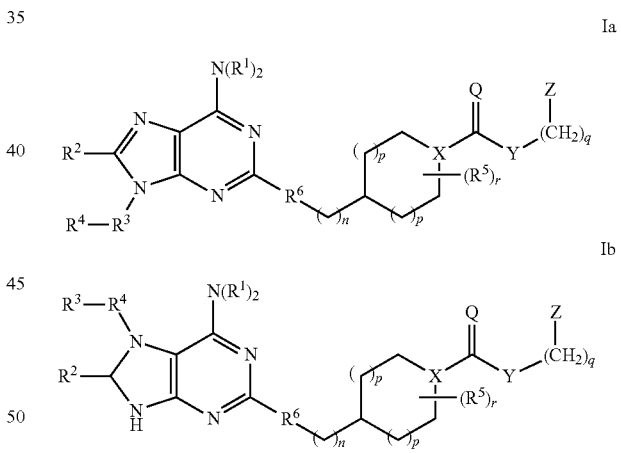

wherein:
the (CH$_2$) portions of (CH$_2$)$_n$ and (CH$_2$)$_q$ are independently substituted with 0-2 groups selected from OH, =O, C$_{1-4}$ alkyl, C$_{3-6}$ cycloalkyl, and benzyl;
Q is O or S;
X is CH or N;
Y is selected from the group consisting of O, NY$^1$, OCH$_2$CH$_2$OCH$_2$, OCH$_2$CH$_2$OCH$_2$CH$_2$OCH$_2$, OCH$_2$CH$_2$OCH$_2$CH$_2$OCH$_2$CH$_2$OCH$_2$, NY$^1$CH$_2$CH$_2$OCH$_2$, NY$^1$CH$_2$CH$_2$OCH$_2$CH$_2$OCH$_2$, and NY$^1$CH$_2$CH$_2$OCH$_2$CH$_2$OCH$_2$CH$_2$OCH$_2$;
alternatively, Y is absent;
Y$^1$ is selected from the group consisting of H, C$_{1-4}$ alkyl, benzyl, C$_{3-6}$ cycloalkyl, and (C$_{3-6}$ cycloalkyl)C$_{1-4}$ alkylene;

Z is selected from the group consisting of aryl and heteroaryl, wherein Z is attached via a carbon atom and is substituted with 1-4 $Z^1$ groups;

$Z^1$ is independently selected from the group consisting of F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, and $OCF_3$;

$R^a$ is independently selected from the group consisting of H, $C_{1-6}$ alkyl, $C_{2-6}$ alkenyl, $C_{2-6}$ alkynyl, $C_{3-8}$ cycloalkyl, $(C_{3-8}$ cycloalkyl$)C_{1-8}$ alkylene, aryl, (aryl)$C_{1-8}$ alkylene, heteroaryl, and (heteroaryl)$C_{1-8}$ alkylene, wherein the alkyl and cycloalkyl optionally are interrupted with 1-2 heteroatoms selected from the group consisting of —O—, —$S(O)_{0-2}$— and —$NR^c$—;

$R^1$ is independently selected from the group consisting of H, $C_{1-8}$ alkyl, $C_{3-8}$ cycloalkyl, $(C_{3-8}$ cycloalkyl$)C_{1-8}$ alkylene, aryl, (aryl)$C_{1-8}$ alkylene, heteroaryl, (heteroaryl)$C_{1-8}$ alkylene, (aryl)(aryl)-$C_{1-8}$ alkylene, (heteroaryl)(heteroaryl)-$C_{1-8}$ alkylene, and (aryl)(heteroaryl)$C_{1-8}$ alkylene, wherein the alkyl and cycloalkyl optionally may be interrupted with 1-2 heteroatoms selected from the group consisting of —O—, —$S(O)_{0-2}$— and —$NR^c$—, and the groups of $R^1$ are substituted with 0-4 groups independently selected from the group consisting of F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, and $OCF_3$;

$R^2$ is selected from the group consisting of H, $C_{1-6}$ alkyl, $OR^a$, $N(R^a)_2$, $C_{3-8}$ cycloalkyl, aryl, heterocycle, and heteroaryl, wherein the alkyl, cycloalkyl, aryl, heterocycle, and heteroaryl optionally are substituted with 1-2 groups independently selected from the group consisting of F, Cl, I, Br, $CH_3$, $CF_3$, and $CH_3O$;

$R^3$ is absent or is $C_{1-8}$ alkylene, wherein the alkylene group optionally is interrupted with 1-2 heteroatoms selected from the group consisting of —O—, —$S(O)_{0-2}$— and —NH—;

$R^3$ is substituted with 0-2 groups selected from the group consisting of F, Cl, Br, I, —$OR^d$, —$SR^d$, —$N(R^d)_2$, $C_{3-6}$ cycloalkyl, $(C_{3-6}$ cycloalkyl$)C_{1-4}$ alkylene, aryl, (aryl)$C_{1-4}$ alkylene, heteroaryl, and (heteroaryl)$C_{1-4}$ alkylene, wherein the alkyl and cycloalkyl optionally are interrupted by 1-2 heteroatoms selected from the group consisting of —O—, —$S(O)_{0-2}$—, and —$NR^c$—;

$R^4$ is selected from the group consisting of $C_{1-8}$ alkyl, $C_{2-8}$ alkenyl, $C_{2-8}$ alkynyl, $C_{3-12}$ cycloalkyl, $(C_{3-12}$ cycloalkyl$)C_{1-8}$ alkylene, aryl, (aryl)$C_{1-8}$ alkylene, heteroaryl, (heteroaryl)$C_{1-8}$ alkylene, $CF_3$, —$CO_2R^b$, $R^bC(O)$—, $(R^b)_2NC(O)$—, $R^bOC(S)$—, $R^bC(S)$—, and $R^bS(=O)$—, wherein the alkyl and cycloalkyl optionally are interrupted with 1-2 heteroatoms selected from the group consisting of —O—, —$S(O)_{0-2}$— and —NH—, and the alkyl, alkenyl, alkynyl, cycloalkyl, aryl, and heteroaryl are substituted with 0-4 groups independently selected from the group consisting of F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, $OCF_3$, and —$OS(O_2)R^a$;

alternatively, when $R^3$ is present, $R^4$ is additionally selected from the group consisting of H, F, Cl, Br, I, $N(R^b)_2$, $OR^b$, $SR^b$, —CN, $N_2$, $CF_3O$, $R^bC(O)O$—, —$OCO_2R^b$, $(R^b)_2NC(O)O$—, $R^bOC(O)NR^b$—, $R^bC(O)NR^b$—, $(R^b)_2NC(O)NR^b$—, and $(R^b)_2NC(S)NR^b$—;

provided that when $R^2$ is H and $R^3$ is absent, then $R^4$ is other than

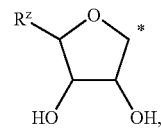

wherein:

(a) "*" is the point of attachment;

(b) $R^z$ is —$CH_2OR$, —$CO_2R$, —$OC(O)R$, —$CH_2OC(O)R$, —$CH_2SR$, —$C(S)OR$, —$CH_2OC(S)R$, —$CH_2NRR$, —$C(S)NRR$, and, —$C(O)NRR$; and, (c) R is H or a substituent;

$R^b$ is independently selected from the group consisting of H, $C_{1-6}$ alkyl, $C_{2-6}$ alkenyl, $C_{2-6}$ alkynyl, $C_{3-8}$ cycloalkyl, $(C_{3-8}$ cycloalkyl$)C_{1-8}$ alkylene, aryl, (aryl)$C_{1-8}$ alkylene, heteroaryl, and (heteroaryl)$C_{1-8}$ alkylene, wherein the alkyl and cycloalkyl optionally are interrupted with 1-2 heteroatoms selected from the group consisting of —O—, —$S(O)_{0-2}$— and —NH— and wherein the alkyl, cycloalkyl, aryl, and heteroaryl are substituted with 0-4 substituents selected from the group consisting of F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aN$-HOH, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, and $OCF_3$;

$R^c$ is independently selected from the group consisting of H, $C_{1-6}$ alkyl, and benzyl;

$R^d$ is independently selected from the group consisting of H, $C_{1-6}$ alkyl, $C_{3-6}$ cycloalkyl, $(C_{3-6}$ cycloalkyl$)C_{1-4}$ alkylene, phenyl, and benzyl;

$R^5$ is independently selected from the group consisting of H, F, Cl, Br, I, —$OR^c$, —$N(R^c)_2$, $C_{1-6}$ alkyl, $C_{3-6}$ cycloalkyl, aryl, and (aryl)$C_{1-4}$ alkylene, wherein the alkyl and cycloalkyl optionally are interrupted by 1-2 heteroatoms selected from the group consisting of —O—, —$S(O)_{0-2}$—, and —$NR^b$—;

$R^6$ is selected from the group consisting of $CH_2CH_2$, $CH=CH$, and $C\equiv C$;

a is independently selected from the group consisting of 0, 1, and 2;

n is independently selected from the group consisting of 0, 1, and 2;

p is independently selected from the group consisting of 0, 1, and 2;

q is independently selected from the group consisting of 0, 1, and 2; and, r is independently selected from the group consisting of 0, 1, and 2.

In another aspect, when $R^2$ is H, $R^5$ is $C\equiv C$, and Y is O or $NY^1$, then at least one $Z^1$ is other than —CN, $OR^a$, and $NR^aNR^a$, wherein $R^a$ is H or $C_{1-6}$ alkyl;

In another aspect, the present invention provides novel compounds of formula IIa or IIIa:

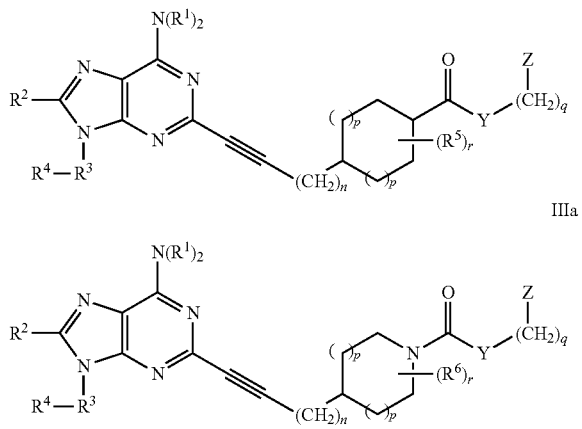

Y is selected from the group consisting of O, NY¹, OCH₂CH₂OCH₂, and, NY¹CH₂CH₂OCH₂;

alternatively, Y is absent;

Y¹ is selected from the group consisting of H and CH₃;

Z is selected from the group consisting of 5-6 membered heteroaryl and phenyl, wherein Z is attached via a carbon atom and is substituted with 1-4 Z¹ groups;

Z¹ is independently selected from the group consisting of F, Cl, $C_{1-4}$ alkyl, $C_{2-4}$ alkenyl, $C_{2-4}$ alkynyl, —(CH₂)$_a$OR$^a$, —(CH₂)$_a$NR$^a$R$^a$, —(CH₂)$_a$NHOH, —(CH₂)$_a$NR$^a$NR$^a$R$^a$, —(CH₂)$_a$NO₂, —(CH₂)$_a$CN, —(CH₂)$_a$CO₂R$^a$, —(CH₂)$_a$C(O)R$^a$, —(CH₂)$_a$OC(O)R$^a$, —(CH₂)$_a$CONR$^a$R$^a$, CF₃, and OCF₃;

R$^a$ is independently selected from the group consisting of H, $C_{1-4}$ alkyl, $C_{2-4}$ alkenyl, $C_{2-4}$ alkynyl, $C_{3-6}$ cycloalkyl, ($C_{3-6}$ cycloalkyl)$C_{1-2}$ alkylene, aryl, (aryl)$C_{1-2}$ alkylene, heteroaryl, and (heteroaryl)$C_{1-2}$ alkylene, wherein the alkyl and cycloalkyl optionally are interrupted with 1-2 heteroatoms selected from the group consisting of —O—, —S(O)$_{0-2}$— and —NR$^c$—;

R¹ is independently selected from the group consisting of H, $C_{1-4}$ alkyl, $C_{3-6}$ cycloalkyl, ($C_{3-6}$ cycloalkyl)$C_{1-4}$ alkylene, aryl, (aryl)$C_{1-4}$ alkylene, heteroaryl, (heteroaryl)$C_{1-4}$ alkylene, (aryl)(aryl)-$C_{1-4}$ alkylene, (heteroaryl)(heteroaryl)-$C_{1-4}$ alkylene, and (aryl)(heteroaryl)$C_{1-2}$ alkylene, wherein the alkyl and cycloalkyl optionally are interrupted with 1-2 heteroatoms selected from the group consisting of —O—, —S(O)$_{0-2}$— and —NR$^c$— and the aryl and heteroaryl rings are substituted with 0-2 groups independently selected from the group consisting of F, Cl, $C_{1-4}$ alkyl, $C_{2-4}$ alkenyl, $C_{2-4}$ alkynyl, —(CH₂)$_a$OR$^a$, —(CH₂)$_a$NR$^a$R$^a$, —(CH₂)$_a$NHOH, —(CH₂)$_a$NR$^a$NR$^a$R$^a$, —(CH₂)$_a$NO₂, —(CH₂)$_a$CN, —(CH₂)$_a$CO₂R$^a$, —(CH₂)$_a$C(O)R$^a$, —(CH₂)$_a$OC(O)R$^a$, —(CH₂)$_a$CONR$^a$R$^a$, CF₃, and OCF₃;

R² is selected from the group consisting of H, $C_{1-4}$ alkyl, OR$^a$, N(R$^a$)₂, $C_{3-6}$ cycloalkyl, aryl, heterocycle, and heteroaryl, wherein the alkyl, cycloalkyl, aryl, heterocycle, and heteroaryl are substituted with 0-2 groups independently selected from the group consisting of F, Cl, CH₃, CF₃, and CH₃O;

R⁴ is selected from the group consisting of $C_{1-4}$ alkyl, $C_{2-4}$ alkenyl, $C_{2-4}$ alkynyl, $C_{3-6}$ cycloalkyl, ($C_{3-6}$ cycloalkyl)$C_{1-2}$ alkylene, aryl, (aryl)$C_{1-2}$ alkylene, heteroaryl, (heteroaryl)$C_{1-2}$ alkylene, CF₃, —CO₂R$^b$, R$^b$C(O)—, (R$^b$)₂NC(O)—, R$^b$OC(S)—, R$^b$C(S)—, and R$^b$S(=O)—, wherein the alkyl and cycloalkyl optionally are interrupted with 1-2 heteroatoms selected from the group consisting of —O—, —S(O)$_{0-2}$— and —NH—, and the alkyl, alkenyl, alkynyl, cycloalkyl, aryl, and heteroaryl are substituted with 0-3 groups independently selected from the group consisting of F, Cl, $C_{1-4}$ alkyl, $C_{2-4}$ alkenyl, $C_{2-4}$ alkynyl, —(CH₂)$_a$OR$^a$, —(CH₂)$_a$NR$^a$R$^a$, —(CH₂)$_a$NHOH, —(CH₂)$_a$NR$^a$NR$^a$R$^a$, —(CH₂)$_a$NO₂, —(CH₂)$_a$CN, —(CH₂)$_a$CO₂R$^a$, —(CH₂)$_a$C(O)R$^a$, —(CH₂)$_a$OC(O)R$^a$, —(CH₂)$_a$CONR$^a$R$^a$, CF₃, OCF₃, and —OS(O₂)R$^a$;

alternatively, when R³ is at least 1, R⁴ additionally may be selected from the group consisting of H, F, Cl, N(R$^b$)₂, OR$^b$, SR$^b$, —CN, NO₂, CF₃O, R$^b$C(O)O—, —OCO₂R$^b$, (R$^b$)₂NC(O)O—, R$^b$OC(O)NR$^b$—, R$^b$C(O)NR$^b$—, (R$^b$)₂NC(O)NR$^b$—, and (R$^b$)₂NC(S)NR$^b$—;

provided that when R² is H and R³ is absent, then R⁴ is other than

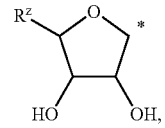

wherein:
(a) "*" is the point of attachment;
(b) R$^z$ is —CH₂OR, —CO₂R, —OC(O)R, —CH₂OC(O)R, —CH₂SR, —C(S)OR, —CH₂OC(S)R, —CH₂NRR, —C(S)NRR, and, —C(O)NRR; and,
(c) R is H or a substituent;

R$^b$ is independently selected from the group consisting of H, $C_{1-4}$ alkyl, $C_{2-4}$ alkenyl, $C_{2-4}$ alkynyl, $C_{3-6}$ cycloalkyl, ($C_{3-6}$ cycloalkyl)$C_{1-2}$ alkylene, aryl, (aryl)$C_{1-2}$ alkylene, heteroaryl, and (heteroaryl)$C_{1-2}$ alkylene, wherein the alkyl and cycloalkyl optionally are interrupted with 1-2 heteroatoms selected from the group consisting of —O—, —S(O)$_{0-2}$— and —NH— and wherein the alkyl, cycloalkyl, aryl, and heteroaryl are substituted with 0-2 substituents selected from the group consisting of F, Cl, $C_{1-4}$ alkyl, $C_{2-4}$ alkenyl, $C_{2-4}$ alkynyl, —(CH₂)$_a$OR$^a$, —(CH₂)$_a$NR$^a$R$^a$, —(CH₂)$_a$NHOH, —(CH₂)$_a$NR$^a$NR$^a$R$^a$, —(CH₂)$_a$NO₂, —(CH₂)$_a$CN, —(CH₂)$_a$CO₂R$^a$, —(CH₂)$_a$C(O)R$^a$, —(CH₂)$_a$OC(O)R$^a$, —(CH₂)$_a$CONR$^a$R$^a$, CF₃, and OCF₃;

R³ is absent or is $C_{1-4}$ alkylene, wherein the alkylene group optionally is interrupted with a heteroatom selected from the group consisting of —O—, —S(O)$_{0-2}$— and —NH—;

R³ is substituted with 0-1 groups selected from the group consisting of F, Cl, —OR$^d$, —SR$^d$, —N(R$^d$)₂, $C_{3-6}$ cycloalkyl, ($C_{3-6}$ cycloalkyl)$C_{1-2}$ alkylene, aryl, (aryl)$C_{1-2}$ alkylene, heteroaryl, and (heteroaryl)$C_{1-2}$ alkylene, wherein the alkyl and cycloalkyl optionally are interrupted by 1-2 heteroatoms selected from the group consisting of —O—, —S(O)$_{0-2}$—, and —NR$^c$—;

R$^c$ is independently selected from the group consisting of H and $C_{1-4}$ alkyl;

R$^d$ is independently selected from the group consisting of H, $C_{1-4}$ alkyl, ($C_{3-6}$ cycloalkyl)$C_{1-2}$ alkylene, and benzyl;

R⁵ is independently selected from the group consisting of H, F, Cl, —OR$^c$, —N(R$^c$)₂, $C_{1-4}$ alkyl, $C_{3-6}$ cycloalkyl, aryl, and (aryl)$C_{1-2}$ alkylene, wherein the alkyl and cycloalkyl optionally are interrupted by 1 heteroatom selected from the group consisting of —O—, —S(O)$_{0-2}$—, and —NR$^b$—;

a is independently selected from the group consisting of 0 and 1;

n is independently selected from the group consisting of 0 and 1;

p is independently selected from the group consisting of 0 and 1;

q is independently selected from the group consisting of 0 and 1; and, r is independently selected from the group consisting of 0 and 1.

In another aspect, the present invention provides novel compounds wherein:

Y is selected from the group consisting of 0 and OCH$_2$CH$_2$OCH$_2$;

alternatively, Y is absent;

Z is selected from the group consisting of phenyl, pyridyl, and pyrimidyl, wherein Z is attached via a carbon atom and is substituted with 1-3 Z$^1$ groups;

Z$^1$ is independently selected from the group consisting of F, Cl, C$_{1-4}$ alkyl, C$_{2-4}$ alkenyl, C$_{2-4}$ alkynyl, OR$^a$, NHOH, NR$^a$NR$^a$R$^a$, NO$_2$, CO$_2$R$^a$, C(O)R$^a$, OC(O)R$^a$, CONR$^a$R$^a$, CF$_3$, and OCF$_3$;

R$^1$ is independently selected from the group consisting of H, C$_{1-4}$ alkyl, (cyclopropyl)CH$_2$—, benzyl, pyridyl-CH$_2$—, (phenyl)(phenyl)-C$_{1-4}$ alkylene, (pyridyl)(pyridyl)-C$_{1-4}$ alkylene, and (phenyl)(pyridyl)C$_{1-4}$ alkylene, wherein the aryl and heteroaryl rings are substituted with 0-2 groups independently selected from the group consisting of F, Cl, CH$_3$, OH, OCH$_3$, NH$_2$, NHCH$_3$, N(CH$_3$)$_2$, NHOH, NHNH$_2$, NO$_2$, CN, CO$_2$CH$_3$, C(O)CH$_3$, CONH$_2$, C(O)NHCH$_3$, C(O)N(CH$_3$)$_2$, CF$_3$, and OCF$_3$;

R$^2$ is selected from the group consisting of H, OR$^a$, N(R$^a$)$_2$, phenyl, and 5-6 membered heteroaryl, wherein the aryl, and heteroaryl are substituted with 0-2 groups independently selected from the group consisting of F, Cl, CH$_3$, CF$_3$, and CH$_3$O;

R$^3$ is absent or is C$_{1-2}$ alkylene;

R$^4$ is selected from the group consisting of C$_{2-4}$ alkenyl, C$_{2-4}$ alkynyl, cyclopropyl, cyclobutyl, cyclopentyl, cyclohexyl, phenyl, naphthyl, heteroaryl, wherein the cycloalkyls optionally are interrupted with a heteroatom selected from the group consisting of —O—, —S(O)$_{0-2}$— and —NH—, and the alkenyl, alkynyl, cycloalkyl, aryl, and heteroaryl are substituted with 0-2 groups independently selected from the group consisting of F, Cl, CH$_3$, OH, OCH$_3$, NH$_2$, NHCH$_3$, N(CH$_3$)$_2$, NHOH, NHNH$_2$, NO$_2$, CN, CO$_2$CH$_3$, C(O)CH$_3$, CONH$_2$, C(O)NHCH$_3$, C(O)N(CH$_3$)$_2$, CF$_3$, and OCF$_3$;

R$^5$ is independently selected from the group consisting of H and CH$_3$;

n is 1;

p is 1;

q is independently selected from the group consisting of 0 and 1; and, r is independently selected from the group consisting of 0 and 1.

In another aspect, the present invention provides novel compounds wherein:

Z is selected from the group consisting of phenyl, pyridyl, and pyrimidyl, wherein Z is attached via a carbon atom and is substituted with 1 Z$^1$ group: and, Z$^1$ is independently selected from the group consisting of F, Cl, CH$_3$, CH$_2$CH$_3$, OH, OCH$_3$, NH$_2$, NHCH$_3$, N(CH$_3$)$_2$, NHOH, NHNH$_2$, NO$_2$, CN, CO$_2$CH$_3$, C(O)CH$_3$, CONH$_2$, C(O)NHCH$_3$, C(O)N(CH$_3$)$_2$, CF$_3$, and OCF$_3$.

In another aspect, the present invention provides novel compounds wherein the compound is of formula IIa.

In another aspect, the present invention provides novel compounds wherein p is 1.

In another aspect, the present invention provides novel compounds wherein r is 0.

In another aspect, the present invention provides novel compounds wherein Y is O.

In another aspect, the present invention provides novel compounds wherein the compound is of formula IIb:

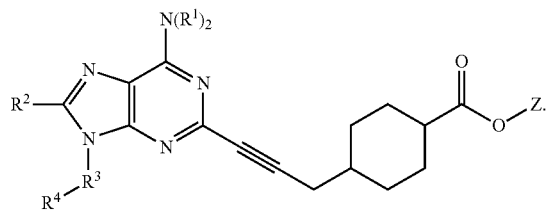

IIb

In another aspect, the present invention provides novel compounds wherein the compound is of formula IIIa.

In another aspect, the present invention provides novel compounds wherein p is 1.

In another aspect, the present invention provides novel compounds wherein r is 0.

In another aspect, the present invention provides novel compounds wherein Y is O.

In another aspect, the present invention provides novel compounds wherein the compound is of formula IIIb:

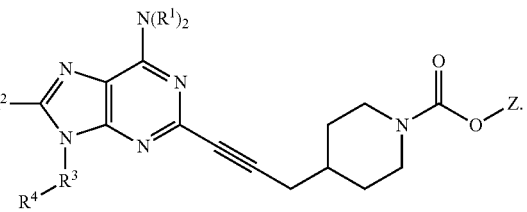

IIIb

In another aspect, the present invention provides novel compounds selected from:
4-[3-(6-Amino-9-prop-2-ynyl-9H-purin-2-yl)-prop-2-ynyl]-piperidine-1-carboxylic acid 2-benzyloxy-ethyl ester;
4-[3-(6-Amino-9-cyclopentyl-9H-purin-2-yl)-prop-2-ynyl]-piperidine-1-carboxylic acid 2-benzyloxy-ethyl ester;
4-[3-(6-Amino-9-prop-2-ynyl-9H-purin-2-yl)-prop-2-ynyl]-piperidine-1-carboxylic acid 3-trifluoromethyl-phenyl ester;
4-[3-(6-Amino-9-cyclopentyl-9H-purin-2-yl)-prop-2-ynyl]-piperidine-1-carboxylic acid 3-trifluoromethyl-phenyl ester;
4-[3-(6-Amino-9-prop-2-ynyl-9H-purin-2-yl)-prop-2-ynyl]-piperidine-1-carboxylic acid 2-fluoro-phenyl ester;
4-[3-(6-Amino-9-prop-2-ynyl-9H-purin-2-yl)-prop-2-ynyl]-piperidine-1-carboxylic acid 4-nitro-phenyl ester;
4-[3-(6-Amino-9-prop-2-ynyl-9H-purin-2-yl)-prop-2-ynyl]-piperidine-1-carboxylic acid 4-methoxycarbonyl-phenyl ester;
4-[3-(6-Amino-9-prop-2-ynyl-9H-purin-2-yl)-prop-2-ynyl]-piperidine-1-carboxylic acid 4-chloro-phenyl ester;
4-[3-(6-Amino-9-prop-2-ynyl-9H-purin-2-yl)-prop-2-ynyl]-piperidine-1-carboxylic acid 4-methoxy-phenyl ester;
4-[3-(6-Amino-9-prop-2-ynyl-9H-purin-2-yl)-prop-2-ynyl]-piperidine-1-carboxylic acid 4-methyl-phenyl ester;
4-[3-(6-Amino-9-prop-2-ynyl-9H-purin-2-yl)-prop-2-ynyl]-piperidine-1-carboxylic acid 4-nitro-benzyl ester;

4-[3-(6-Amino-9-prop-2-ynyl-9H-purin-2-yl)-prop-2-ynyl]-piperidine-1-carboxylic acid 2-chloro-phenyl ester;
4-[3-(6-Amino-9-prop-2-ynyl-9H-purin-2-yl)-prop-2-ynyl]-piperidine-1-carboxylic acid 2-methoxy-phenyl ester;
2-{3-[1-((3,4-Dimethyl)phenoxycarbanoyl)piperidin-4-yl]propyn-1-yl}-9-propargyladenine;
2-{3-[1-((3,4-Difluoro)phenoxycarbanoyl)piperidin-4-yl]propyn-1-yl}-9-propargyladenine; and,
2-{3-[1-((3,4-Dichloro)phenoxycarbanoyl)piperidin-4-yl]propyn-1-yl}-9-propargyladenine.

In another aspect of the invention, there is provided a pharmaceutical composition, comprising: a therapeutically effective amount of a compound of the present invention and a pharmaceutically acceptable carrier.

In another aspect of the invention, there is provided a therapeutic method for treating a pathological condition or symptom in a mammal, wherein the activity of adenosine $A_{2A}$ receptors is implicated and antagonism of its action is desired, comprising: administering to the mammal a therapeutically effective amount of a compound of the present invention.

In another aspect of the invention, there is provided a method of treating a disease, comprising: administering a therapeutically effective amount of at least one compound of the present invention or a stereoisomer or pharmaceutically acceptable salt thereof, wherein the disease is selected from movement disorders, cancer, and addictive disorders (e.g., smoking, alcohol, drugs).

In another aspect of the invention, the movement disorder is selected from: Huntington's disease, catalepsy, Parkinson's disease, narcolepsy, progressive supernuclear palsy, multiple system atrophy, corticobasal degeneration, Wilson's disease, Hallervorden-Spatz disease, progressive pallidal atrophy, Dopa-responsive dystonia-Parkinsonism, and spasticity.

In another aspect of the invention, there is provided a therapeutic method for preventing or treating a pathological condition or symptom in a mammal, wherein the activity of adenosine $A_{2A}$ receptors is implicated and antagonism of receptor action is desired, comprising administering to the mammal an effective amount of a compound of the present invention.

In another aspect of the invention, there is provided the compound of the present invention for use in medical therapy.

In another aspect, there is provided a use of a compound of the invention, for the manufacture of a medicament useful for the treatment of a disease in a mammal.

Any aspect or feature of the present invention whether characterized as preferred or not characterized as preferred may be combined with any other aspect or feature of the invention, whether such other feature is characterized as preferred or not characterized as preferred.

When $R^4$-$R^3$- is H, then the imidazole ring of the compounds of the present invention may exist in tautomeric forms or as tautomers (e.g., the alkynyl substituent can be located at the 7- or 9-position). The skilled artisan will recognize that these tautomers are included within the scope of the present invention. By naming or referring to one compound, for example, its corresponding tautomer is also intended.

DEFINITIONS

The examples provided in this application are non-exclusive unless otherwise stated. They include, but are not limited to, the recited groups.

The indefinite articles "a" and "an" mean "at least one" or "one or more" when used in this application, including the claims, unless specifically indicated otherwise.

Examples of the molecular weight of compounds of the present invention can include (a) less than about 500, 550, 600, 650, 700, 750, 800, 850, 900, 950, or 1000 grams per mole; (b) less than about 950 grams per mole; (c) less than about 850 grams per mole, and, (d) less than about 750 grams per mole.

The term "substituted" means that any one or more hydrogens on the designated group (or atom) is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. If more than one substitutent is allowed (e.g., 0-4), then each number of the range is individually included. For example, (a) 0-4, includes 0, 1, 2, 3, and 4, and (b) 0-2 includes 0, 1, and 2.

Stable means that the compound is suitable for pharmaceutical use.

The present invention covers stable compound and thus avoids, unless otherwise specified, the following bond types: heteroatom-halogen, N—S, O—S, O—O, and S—S The present invention includes all isotopes of atoms occurring in the present compounds. Isotopes include those atoms having the same atomic number but different mass numbers. Isotopes of hydrogen include tritium and deuterium. Isotopes of carbon include C-13 and C-14.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl. When alkyl is interrupted by an NH, the NH group can be substituted if a substituent is defined for the alkyl group.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Halo" or "halogen" refers to fluoro, chloro, bromo, and iodo.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups. Cycloalkyl also includes bicycloalkyl and tricycloalkyl, both of which include fused and bridged rings (e.g., norbornane and adamantane). The cycloalkyl group may also be unsaturated though not aromatic (e.g., 1-2 double bonds). Examples of unsaturated cycloalkyl include cyclopentenyl and cyclohexenyl. When cycloalkyl is interrupted by an NH, the NH group can be substituted if a substituent is defined for the alkyl group.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, and tetrahydronaphthyl.

"Heterocycle" refers to any stable ring have the number of specified atoms or a 3, 4, 5, 6, 7, 8, 9, 10, 11, or 12 membered monocyclic, bicyclic, or tricyclic ring that is saturated or partially unsaturated (i.e., non-aromatic), which consists of carbon atoms and 1, 2, 3, or 4 heteroatoms independently selected from the group consisting of N, O and S. As an example, if a heterocycle is 5-6 membered, then it consists of carbon atoms and 1-2 heteroatoms independently selected from the group consisting of N, O and S. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms may optionally be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable. Typically, when the total number of S and O atoms in the heterocycle exceeds 1, then these heteroatoms are not adjacent to one another. Examples of heterocycles include those where the total number of S and O atoms in the heterocycle is 0-1. Examples of heterocycles include decahydroquinolinyl, dihydrofuran, imidazolidinyl, imidazolinyl, morpholinyl, piperidinyl, pyrrolidinyl, and tetrahydrofuranyl. Also included are fused ring and spiro compounds containing, for example, the above heterocycles.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, 4, 5, or 6 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then at least one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Mammal and patient covers warm blooded mammals that are typically under medical care (e.g., humans and domesticated animals). Examples of mammals include (a) feline, canine, equine, bovine, and human and (b) human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting its development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are desirable. Lists of suitable salts are found in *Remington's Pharmaceutical Sciences,* 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat an indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

The compounds of the present invention may have one or more asymmetric centers and may exist in and be isolated in optically active and racemic forms. Some compounds may exhibit polymorphism. The present invention encompasses any racemic, optically-active, polymorphic, or stereoisomeric form, or mixtures thereof, of a compound of the invention, which possess the useful properties described herein; it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine therapeutic activity using the standard tests described herein or using other similar tests which are well known in the art.

Examples of stereoisomers of the present invention include compounds of formulae A-F (as well as the tautomeric forms, which are not shown).

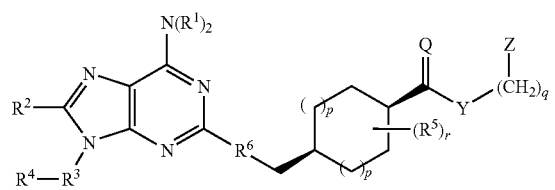

A

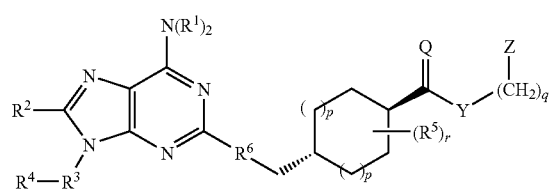

B

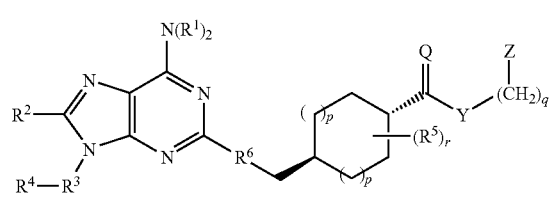

C

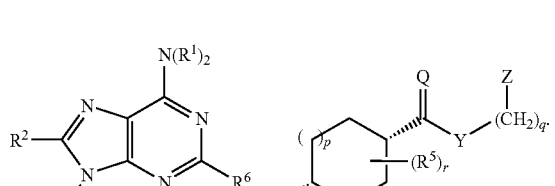

D

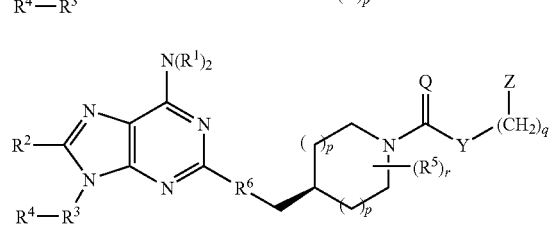

E

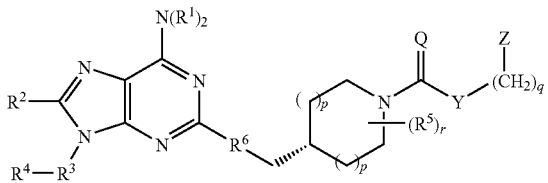

F

Specific values listed for radicals, substituents, and ranges, are for illustration only; they do not exclude other defined values or other values within defined ranges for the radicals and substituents.

DOSAGE AND FORMULATION

The compounds of the present invention can be formulated as pharmaceutical compositions and administered to a mammalian host, such as a human patient in a variety of forms adapted to the chosen route of administration, e.g., orally or parenterally, by intravenous, intramuscular, topical, inhalation or subcutaneous routes. Exemplary pharmaceutical compositions are disclosed in "Remington: The Science and Practice of Pharmacy", A. Gennaro, ed., 20th edition, Lippincott, Williams & Wilkins, Philadelphia, Pa.

The present compounds may be systemically administered, e.g., orally, in combination with a pharmaceutically acceptable carrier such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more carriers and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; carriers such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. It will be understood that any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it may be desirable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, desirable methods of preparation include vacuum drying and freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from (a) about 0.1-25 wt % and (b) about 0.5-10 wt %. The concentration in a semi-solid or solid composition such as a gel or a powder will be (a) about 0.1-5 wt % and (b) about 0.5-2.5 wt %.

The amount of the compound or an active salt or derivative thereof, required for use in treatment will vary not only with the particular compound or salt selected but also with the route of administration, the nature of the condition being treated, and the age and condition of the patient and will be ultimately at the discretion of the attendant physician or clinician. In general, however, a suitable dose will be in the range of from (a) about 1.0-100 mg/kg of body weight per day, (b) about 10-75 mg/kg of body weight per day, and (c) about 5-20 mg/kg body weight per day.

The compound can be conveniently administered in unit dosage form; e.g., tablets, caplets, etc., containing (a) about 4-400 mg, (b) about 10-200 mg, and (c) about 20-100 mg of active ingredient per unit dosage form.

Ideally, the active ingredient should be administered to achieve peak plasma concentrations of the active compound of from (a) about 0.02-20 µM, (b) about 0.1-10 µM, and (c) about 0.5-5 µM. These concentrations may be achieved, for example, by the intravenous injection of a 0.005-0.5% solution of the active ingredient, or orally administered as a bolus containing about 4-400 mg of the active ingredient.

The compounds of the invention can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) (Mack Publishing Co.)

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All patents, patent applications, books and literature cited in the specification are hereby incorporated by reference in their entirety. In the case of any inconsistencies, the present disclosure, including any definitions therein will prevail.

The invention has been described with reference to various specific and detailed aspects and techniques. However, it should be understood that many variations and modifications may be made while remaining within the spirit and scope of the invention. The present invention, thus generally described, will be understood more readily by reference to the following examples, which are provided by way of illustration and are not intended to be limiting of the present invention.

EXAMPLES

Pharmacology

The ability of compounds of the invention to act as an $A_{2A}$ adenosine receptor antagonist may be determined using pharmacological models which are well known in the art (e.g., see United States Patent Application Publication No. 2005/0282831).

Compounds of the present invention are expected to be $A_{2A}$ adenosine receptor antagonists. Compounds of the present invention are considered to be $A_{2A}$ adenosine receptor antagonists if they have an $IC_{50}$ value less than or equal to 1 μM. Representative compounds have been tested and have been shown to be active as their $IC_{50}$ values were found to be in the range of $\leq 1$ μM. Additional examples of desirable activity levels of $A_{2A}$ adenosine receptor antagonists useful in the present invention include (a) an $IC_{50}$ value of 0.1 μM or lower, (b) an $IC_{50}$ value of 0.01 μM or lower, (c) an $IC_{50}$ value of 0.001 μM or lower, and (d) an $IC_{50}$ value of 0.0001 μM or lower.

It can also be beneficial for the compounds of the present invention to be selective for the $A_{2A}$ receptor versus the other adenosine receptors $A_1$, $A_{2B}$, and $A_3$. A 3-fold selectivity for $A_{2A}$ versus $A_1$, would be, for example, 100 nM for $A_{2A}$ and 300 nM for $A_1$ (300/100=3). Examples of selectivity for $A_{2A}$ versus $A_1$ include (a) at least 3-fold for $A_{2A}$; (b) at least 4-fold for $A_{2A}$; (c) at least 5-fold for $A_{2A}$; (d) at least 10-fold for $A_{2A}$; (e) at least 20-fold for $A_{2A}$; and, (f) at least 100-fold for $A_{2A}$. Examples of selectivity for $A_{2A}$ versus $A_{2B}$ include (a) at least 3-fold for $A_{2A}$; (b) at least 4-fold for $A_{2A}$; (c) at least 5-fold for $A_{2A}$; (d) at least 10-fold for $A_{2A}$; (e) at least 20-fold for $A_{2A}$; and, (f) at least 100-fold for $A_{2A}$. Examples of selectivity for $A_{2A}$ versus $A_3$ include (a) at least 3-fold for $A_{2A}$; (b) at least 4-fold for $A_{2A}$; (c) at least 5-fold for $A_{2A}$; (d) at least 10-fold for $A_{2A}$; (e) at least 20-fold for $A_{2A}$; and, (f) at least 100-fold for $A_{2A}$.

Examples of the present invention are shown below in Table A.

TABLE A

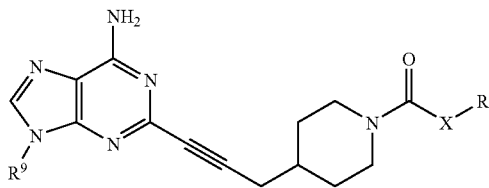

| Ex. No. | R | X | $R^9$ |
|---|---|---|---|
| 1* | Phenyl | O | Propargyl |
| 2* | Phenyl | O | Cyclopentyl |
| 3 | —CH$_2$CH$_2$OBn | O | Propargyl |
| 4 | —CH$_2$CH$_2$OBn | O | Cyclopentyl |
| 5 | 3-Trifluoromethylphenyl | O | Propargyl |
| 6 | 3-Trifluoromethylphenyl | O | Cyclopentyl |
| 7 | 4-Fluorophenyl | O | Propargyl |
| 8 | 4-Nitrophenyl | O | Propargyl |
| 9 | (4-benzoyloxy group structure) | O | Propargyl |
| 10 | 4-Chlorophenyl | O | Propargyl |
| 11 | 4-Methoxyphenyl | O | Propargyl |
| 12 | 4-Methylphenyl | O | Propargyl |
| 13 | 4-Nitrobenzyl | O | Propargyl |
| 14 | 2-Chlorophenyl | O | Propargyl |
| 15 | 2-Methoxyphenyl | O | Propargyl |
| 16 | 3,4-Dimethylphenyl | O | Propargyl |
| 17 | 3,4-Difluorophenyl | O | Propargyl |
| 18 | 3,4-Dichlorophenyl | O | Propargyl |

*Examples 1 and 2 are for comparative purposes.

Synthesis and Characterization

Proton nuclear magnetic resonance spectroscopy was performed on a Varian-300 MHz spectrometer and spectra were taken in solution using either CD$_3$OD, CDCl$_3$, or DMSO-d$_6$ as solvent Unless noted, chemical shifts are expressed as ppm downfield from CD$_3$OD (3.30 ppm), CDCl$_3$ (7.26 ppm) or DMSO-d$_6$ (2.5 ppm). Electro-spray-ionization (ESI) mass spectrometry was performed with a ThermoFinnigan LCQ mass spectrometer.

Representative Procedure for N6-Amino Substitution

2-Iodoadenosine

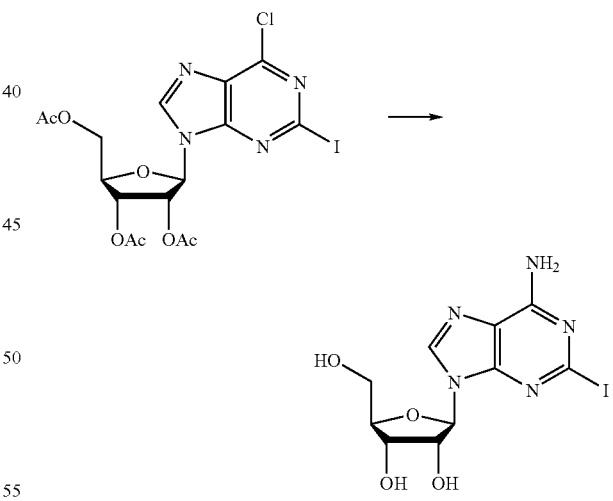

A suspension of 6-chloro-2-iodo-9-(2',3',5'-O-triacetyl-furanosyl)-9H-purine (14.70 g, 0.02729 mol) in MeOH (300 mL) was cooled over an ice bath. Ammonia gas was then bubbled through the mixture until it was saturated. The reaction vessel was sealed and heated at 40° C. for 18 h and at 60° C. for 5 days. The mixture was cooled over ice and nitrogen gas bubbled through the solution, the mixture being allowed to warm to room temperature. The solvent was then removed under reduced pressure and the crude recrystallized from water containing 3-4 drops of glacial acetic acid. The resulting precipitate was filtered and washed with water and ether to afford a white solid: yield 7.167 g, 67%.

Representative Procedure for C2 Coupling

2-{(3-[1-((2-Chloro)phenoxycarbanoyl)piperidin-4-yl]propyn-1-yl}adenosine

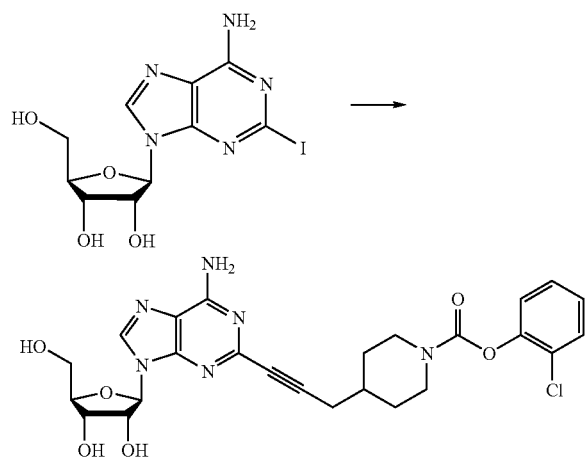

To a solution of 2-iodoadenosine (0.602 g, 1.531 mmol) in freshly degassed DMF (20 mL) was added degassed triethylamine (1.20 mL, 8.54 mmol), Pd(PPh₃)₄ (85 mg, 0.074 mmol), CuI (catalytic), and 2-chlorophenyl 4-(prop-2-ynyl)piperidine-1-carboxylate (0.588 g, 2.117 mmol). The mixture was stirred at room temperature under and inert atmosphere for 20 h. Silica bound Pd(II) scavenger Si-thiol (400 mg) and Pd(0) scavenger Si-TAAcOH (619 mg) were added and stirring continued a further 72 h. The suspension was filtered through celite and the resulting solution evaporated to dryness. The crude was purified by column chromatography, eluting with a gradient of DCM/MeOH (0-4%) to afford the pure product as a white solid: yield 0.733 g, 88%.

Representative Procedure for Ribose Cleavage

4-[3-(6-Amino-9H-purin-2-yl)-prop-2-ynyl]-piperidine-1-carboxylic acid 2-chloro-phenyl Ester

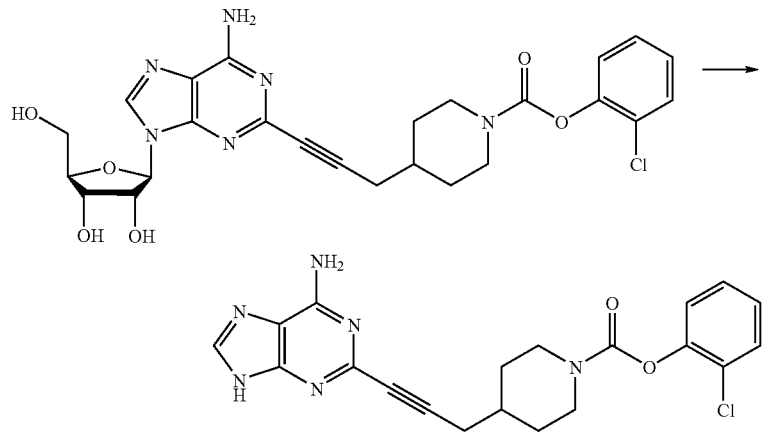

A solution of 2-{3-[1-((2-chloro)phenoxycarbanoyl)piperidin-4-yl]propyn-1-yl}adenosine (0.720 g, 1.326 mmol) in methanol (25 mL) and 1.0 M HCl (2.50 mL) was stirred at 90° C. in a pressure apparatus for 22 h. The pH was adjusted to 5 with 1.0 M NaOH and the methanol removed under reduced pressure. After cooling the resulting precipitate was filtered and washed with water to afford the pure product as a white solid: yield 1.481 g, 88%.

Representative Procedure for N9-Alkylation Using an Appropriate Alkyl Halide or Alkyl Tosylate:

An appropriate 9-unsubstituted adenine (0.099 mmol) was dissolved in DMF (10 mL). Anhydrous potassium carbonate (38 mg, 0.275 mmol) and an appropriate alkyl halide (0.121 mmol) or alkyl tosylate were added and the mix stirred at 25-100° C. for 17-71 h. The reaction mixture was adhered to silica and purified by column chromatography, eluting with a gradient of DCM/MeOH (0-6%) to afford the pure product.

Example 1

4-[3-(6-Amino-9-prop-2-ynyl-9H-purin-2-yl)-prop-2-ynyl]-piperidine-1-carboxylic Acid Phenyl Ester Using the representative procedure for N9-alkylation above 4-[3-(6-amino-9H-purin-2-yl)-prop-2-ynyl]-piperidine-1-carboxylic acid phenyl ester (42 mg) gave the title compound as a white solid: yield 16 mg, 35%. ¹H NMR (CD₃OD) δ 8.21 (s, 1H), 7.39-7.32, 7.22-7.16, 7.10-7.06 (3×m, 5H), 5.03 (d, 2H, J=2.6 Hz), 4.41-4.12 (m, 2H), 3.07, 2.93 (2×m, 2H), 2.98 (t, 1H, J=2.6 Hz), 2.49 (d, 2H, J=6.2 Hz), 2.02-1.81, 1.53-1.33 (2×m, 5H). ¹³C NMR (CD₃OD) δ 157.1, 155.5, 152.9, 150.5, 147.9, 142.6, 130.3, 126.4, 122.9, 119.3, 86.3, 82.5, 77.6, 75.9, 45.7, 45.4, 36.5, 33.9, 32.6, 32.3, 26.5. LRMS ESI (M+H⁺) 415.2.

Example 2

4-[3-(6-Amino-9-cyclopentyl-9H-purin-2-yl)-prop-2-ynyl]-piperidine-1-carboxylic Acid Phenyl Ester Using the representative procedure for N9-alkylation above 4-[3-(6-amino-9H-purin-2-yl)-prop-2-ynyl]-piperidine-1-carboxylic acid phenyl ester (47 mg) gave the title compound as a white solid: yield 30 mg, 53%. ¹H NMR (CD₃OD) δ 8.20 (s, 1H), 7.39-7.32, 7.23-7.16, 7.11-7.06 (3×m, 5H), 4.90 (m, 1H), 4.42-4.14 (m, 2H), 3.08, 2.93 (2×m, 2H), 2.49 (d, 2H, J=6.3 Hz), 2.32-1.18, 2.07-1.73, 1.55-1.32

(3×m, 13H). ¹³C NMR (CD₃OD) δ 157.0, 155.5, 152.9, 150.9, 147.5, 141.2, 130.3, 126.4, 122.9, 119.7, 85.9, 82.7, 57.5, 45.7, 45.5, 36.6, 33.6, 32.6, 32.4, 26.5, 24.8. LRMS ESI (M+H⁺) 445.2.

Example 3

4-[3-(6-Amino-9-prop-2-ynyl-9H-purin-2-yl)-prop-2-ynyl]-piperidine-1-carboxylic acid 2-benzyloxy-ethyl Ester Using the representative procedure for N9-alkylation above 4-[3-(6-Amino-9H-purin-2-yl)-prop-2-ynyl]-piperidine-1-carboxylic acid 2-benzyloxy-ethyl ester (25 mg) gave the title compound as a white solid: yield 20 mg, 74%. ¹H NMR (CD₃OD) δ 8.20 (s, 1H), 7.32-7.20 (m, 5H), 5.01 (d, 2H, J=2.6 Hz), 4.53 (s, 2H), 4.27-4.09 (m, 4H), 3.67 (t, 2H, J=4.7 Hz), 2.98 (t, 1H, J=2.6 Hz), 2.91-2.73 (m, 2H), 2.42 (d, 2H, J=6.3 Hz), 2.91-1.73, 1.37-1.20 (2×m, 5H). ¹³C NMR (CD₃OD) δ 157.0 (×2), 150.4, 147.9, 142.5, 139.5, 129.4, 128.8, 128.7, 119.3, 86.3, 82.5, 77.6, 75.9, 74.0, 69.5, 65.8, 45.1, 36.6, 33.9, 32.5, 26.5. LRMS ESI (M+H⁺) 473.2.

Example 4

4-[3-(6-Amino-9-cyclopentyl-9H-purin-2-yl)-prop-2-ynyl]-piperidine-1-carboxylic acid 2-benzyloxy-ethyl Ester Using the representative procedure for N9-alkylation above 4-[3-(6-amino-9H-purin-2-yl)-prop-2-ynyl]-piperidine-1-carboxylic acid 2-benzyloxy-ethyl ester (21 mg) gave the title compound as a white solid: yield 10 mg, 41%. ¹H NMR (CD₃OD) δ 8.19 (s, 1H), 7.33-7.20 (m, 5H), 4.88 (m, 1H), 4.53 (s, 2H), 4.29-4.10 (m, 4H), 3.67 (t, 2H, J=4.7 Hz), 2 83 (m, 2H), 2.42 (d, 2H, J=6.0 Hz), 2.30-2.16, 2.05-1.70, 1.38-1.21 (3×m, 13H). ¹³C NMR (CD₃OD) δ 157.0 (×2), 150.9, 147.5, 141.4, 139.5, 129.4, 128.8, 128.7, 119.7, 85.9, 82.7, 74.0, 69.5, 65.8, 57.5, 45.1, 36.6, 33.6, 32.5, 26.5, 24.8. LRMS ESI (M+H⁺) 503.4.

Example 5

4-[3-(6-Amino-9-prop-2-ynyl-9H-purin-2-yl)-prop-2-ynyl]-piperidine-1-carboxylic acid 3-trifluoromethyl-phenyl Ester Using the representative procedure for N9-alkylation above 4-[3-(6-Amino-9H-purin-2-yl)-prop-2-ynyl]-piperidine-1-carboxylic acid 3-trifluoromethyl-phenyl ester (48 mg) gave the title compound as a white solid: yield 34 mg, 65%. ¹H NMR (CD₃OD) δ 8.21 (s, 1H), 7.60-7.35 (m, 4H), 5.03 (d, 2H, J=2.6 Hz), 4.40-4.29, 4.25-4.14 (2×m, 2H), 3.08, 2.93 (2×m, 2H), 2.98 (t, 1H, J=2.6 Hz), 2.48 (d, 2H, J=6.5 Hz), 2.01-1.80, 1.54-1.33 (2×m, 5H). ¹³C NMR (CD₃OD) δ 157.1, 154.7, 153.2, 150.5, 147.9, 142.6, 132.7 (q), 131.3, 126.8, 123.4, 123.1, 120.1, 119.3, 86.2, 82.6, 77.6, 75.9, 45.8, 45.5, 36.5, 33.9, 32.6, 32.3, 26.5. LRMS ESI (M+H⁺) 483.3.

Example 6

4-[3-(6-Amino-9-cyclopentyl-9H-purin-2-yl)-prop-2-ynyl]-piperidine-1-carboxylic acid 3-trifluoromethyl-phenyl Ester Using the representative procedure for N9-alkylation above 4-[3-(6-amino-9H-purin-2-yl)-prop-2-ynyl]-piperidine-1-carboxylic acid 3-trifluoromethyl-phenyl ester (38 mg) gave the title compound as a white solid: yield 16 mg, 37%. ¹H NMR (CD₃OD) δ 8.20 (s, 1H), 7.61-7.35 (m, 4H), 4.89 (m, 1H), 4.35, 4.20 (2×m, 2H), 3.09, 2.94 (2×m, 2H), 2.48 (d, 2H, J=6.3 Hz), 2.32-2.17, 2.06-1.72, 1.55-1.34 (3×m, 13H). ¹³C NMR (CD₃OD) δ 157.0, 154.7, 153.2, 150.9, 147.4, 141.4, 132.7 (q), 131.3, 126.8, 123.4, 123.1, 120.1, 119.7, 85.9, 82.7, 57.5, 45.8, 45.5, 36.5, 33.6, 32.3, 26.5, 24.8. LRMS ESI (M+H⁺) 513.4.

Example 7

4-[3-(6-Amino-9-prop-2-ynyl-9H-purin-2-yl)-prop-2-ynyl]-piperidine-1-carboxylic acid 2-fluoro-phenyl Ester Using the representative procedure for N9-alkylation above 4-[3-(6-amino-9H-purin-2-yl)-prop-2-ynyl]-piperidine-1-carboxylic acid 4-fluoro-phenyl ester (77 mg) gave the title compound as a white solid: yield 50 mg, 59%. ¹H NMR (CD₃OD) δ 8.21 (s, 1H), 7.10 (s, 2H), 7.07 (d, 2H, J=1.6 Hz), 5.03 (d, 2H, J=2.6 Hz), 4.32, 4.19 (2×m, 2H), 3.06, 2.91 (2×m, 2H), 2.98 (t, 1H, J=2.6 Hz), 2.48 (d, 2H, J=6.3 Hz), 2.00-1.80, 1.52-1.31 (2×m, 5H). ¹³C NMR (CD₃OD) δ 163.1, 159.9, 157.1, 155.4, 150.5, 148.9 (d), 147.9, 142.6, 124.6, 124.4, 119.3, 116.9, 116.6, 86.2, 82.6, 77.6, 75.9, 45.7, 45.4, 36.5, 33.9, 32.6, 32.3, 26.5. LRMS ESI (M+H⁺) 433.2.

Example 8

4-[3-(6-Amino-9-prop-2-ynyl-9H-purin-2-yl)-prop-2-ynyl]-piperidine-1-carboxylic acid 4-nitro-phenyl Ester Using the representative procedure for N9-alkylation above 4-[3-(6-Amino-9H-purin-2-yl)-prop-2-ynyl]-piperidine-1-carboxylic acid 4-nitro-phenyl ester (64 mg) gave the title compound as a white solid: yield 29 mg, 42%. ¹H NMR (CDCl₃) δ 8.23 (d, 2H), 8.08 (s, 1H), 7.29 (d, 2H), 6.44 (br s, 2H), 4.98 (d, 2H), 4.29 (m, 2H), 3.03, 2.89 (2×m, 2H), 2.55 (t, 1H), 2.52 (d, 2H), 2.05-1.85, 1.51-1.32 (2×m, 5H). ¹³C NMR (CDCl₃) δ 156.4, 154.6, 152.2, 149.5, 145.3, 144.8, 140.7, 125.0, 122.2, 118.7, 86.5, 80.8, 77.2, 75.5, 44.8, 44.4, 35.1, 33.3, 31.7, 31.3, 26.1. LRMS ESI (M+H⁺) 460.2.

Example 9

4-[3-(6-Amino-9-prop-2-ynyl-9H-purin-2-yl)-prop-2-ynyl]-piperidine-1-carboxylic acid 4-methoxycarbonyl-phenyl Ester Using the representative procedure for N9-alkylation above 4-[3-(6-amino-9H-purin-2-yl)-prop-2-ynyl]-piperidine-1-carboxylic acid 4-methoxycarbonyl-phenyl ester (57 mg) gave the title compound as a white solid: yield 34 mg, 55%. ¹H NMR (CDCl₃) δ 8.06 (s, 1H), 8.02 (d, 2H, J=8.7 Hz), 7.17 (d, 2H, J=8.8 Hz), 6.36 (br s, 2H), 4.97 (d, 2H, J=2.6), 4.29 (m, 2H), 3.89 (s, 3H), 2.99, 2.86 (2×m, 2H), 2.54 (t, 1H, J=2.6 Hz), 2.48 (d, 2H, J=6.5 Hz), 2.02-1.82, 1.49-1.30 (2×m, 5H). ¹³C NMR (CDCl₃) δ 166.4, 155.2, 154.9, 152.8, 149.5, 145.8, 140.5, 130.9, 126.9, 121.5, 118.7, 86.1, 81.1, 75.6, 75.4, 52.0, 44.6, 44.3, 35.2, 33.2, 31.7, 31.4, 26.2. LRMS ESI (M+H⁺) 473.2.

Example 10

4-[3-(6-Amino-9-prop-2-ynyl-9H-purin-2-yl)-prop-2-ynyl]-piperidine-1-carboxylic acid 4-chloro-phenyl Ester Using the representative procedure for N9-alkylation above 4-[3-(6-amino-9H-purin-2-yl)-prop-2-ynyl]-piperidine-1-carboxylic acid 4-chloro-phenyl ester (41 mg) gave the title compound as a white solid: yield 30 mg, 67%. $^1$H NMR (CD$_3$OD) δ 8.21 (s, 1H), 7.34 (d, 2H, J=8.9 Hz), 7.09 (d, 2H, J=8.9 Hz), 5.02 (d, 2H, J=2.6 Hz), 4.31, 4.18 (2×m, 2H), 3.06, 2.91 (2×m, 2H), 2.98 (t, 1H, J=2.6 Hz), 2.47 (d, 2H, J=6.3 Hz), 2.00-1.79, 1.51-1.31 (2×m, 5H). $^{13}$C NMR (CD$_3$OD) δ 157.1, 155.0, 151.6, 150.4, 147.9, 142.6, 131.7, 130.3, 124.5, 119.3, 86.2, 82.5, 77.6, 75.9, 45.7, 45.4, 36.5, 33.9, 32.6, 32.3, 26.5. LRMS ESI (M+H$^+$) 449.1.

Example 11

4-[3-(6-Amino-9-prop-2-ynyl-9H-purin-2-yl)-prop-2-ynyl]-piperidine-1-carboxylic acid 4-methoxy-phenyl Ester Using the representative procedure for N9-alkylation above 4-[3-(6-amino-9H-purin-2-yl)-prop-2-ynyl]-piperidine-1-carboxylic acid 4-methoxy-phenyl ester (39 mg) gave the title compound as a white solid: yield 32 mg, 75%. $^1$H NMR (CD$_3$OD) δ 8.21 (s, 1H), 6.98 (d, 2H, J=9.1 Hz), 6.87 (d, 2H, J=9.1 Hz), 5.02 (d, 2H, J=2.5 Hz), 4.32, 4.18 (2×m, 2H), 3.76 (s, 3H), 3.04, 2.89 (2×m, 2H), 2.99 (t, 1H, J=2.6 Hz), 2.47 (d, 2H, J=6.3 Hz), 2.00-1.79, 1.51-1.30 (2×m, 5H). $^{13}$C NMR (CD$_3$OD) δ 158.6, 157.1, 155.9, 150.4, 147.9, 146.3, 142.5, 123.6, 119.3, 115.3, 86.3, 82.5, 77.6, 75.9, 56.1, 45.6, 45.4, 36.5, 33.9, 32.6, 32.3, 26.5. LRMS ESI (M+H$^+$) 445.2.

Example 12

4-[3-(6-Amino-9-prop-2-ynyl-9H-purin-2-yl)-prop-2-ynyl]-piperidine-1-carboxylic acid 4-methyl-phenyl Ester Using the representative procedure for N9-alkylation above 4-[3-(6-amino-9H-purin-2-yl)-prop-2-ynyl]-piperidine-1-carboxylic acid 4-methyl-phenyl ester (38 mg) gave the title compound as a white solid: yield 27 mg, 65%. $^1$H NMR (CD$_3$OD) δ 8.21 (s, 1H), 7.14 (d, 2H, J=8.5 Hz), 6.94 (d, 2H, J=8.4 Hz), 5.02 (d, 2H, J=2.6 Hz), 4.33, 4.19 (2×m, 2H), 3.05, 2.90 (2×m, 2H), 2.98 (t, 1H, J=2.6 Hz), 2.47 (d, 2H, J=6.3 Hz), 2.00-1.79, 1.51-1.32 (2×m, 5H). $^{13}$C NMR (CD$_3$OD) δ 157.1, 155.7, 150.6, 150.4, 147.9, 142.5, 136.2, 130.7, 122.6, 119.3, 86.3, 82.5, 77.6, 75.9, 45.6, 45.4, 36.5, 33.9, 32.6, 32.3, 26.5, 20.8. LRMS ESI (M+H$^+$) 429.2.

Example 13

4-[3-(6-Amino-9-prop-2-ynyl-9H-purin-2-yl)-prop-2-ynyl]-piperidine-1-carboxylic acid 4-nitro-benzyl Ester Using the representative procedure for N9-alkylation above 4-[3-(6-amino-9H-purin-2-yl)-prop-2-ynyl]-piperidine-1-carboxylic acid 4-nitro-benzyl ester (43 mg) gave the title compound as a white solid: yield 37 mg, 79%. $^1$H NMR (CD$_3$OD) δ 8.24 (d, 2H, J=8.8 Hz), 8.21 (s, 1H), 7.59 (d, 2H, J=8.9 Hz), 5.24 (s, 2H), 5.02 (d, 2H, J=2.5 Hz), 4.22 (m, 2H), 2.98 (t, 1H, J=2.6 Hz), 2.91 (m, 2H), 2.46 (d, 2H, J=6.2 Hz), 1.96-1.78, 1.43-1.26 (2×m, 5H). $^{13}$C NMR (DMSO) δ 155.7, 154.0, 149.1, 146.9, 145.8, 144.9, 140.8, 128.0, 123.5, 117.9, 83.4, 82.4, 78.2, 75.9, 64.9, 43.4, 34.5, 32.2, 30.9, 24.8. LRMS ESI (M+H$^+$) 474.2.

Example 14

4-[3-(6-Amino-9-prop-2-ynyl-9H-purin-2-yl)-prop-2-ynyl]-piperidine-1-carboxylic acid 2-chloro-phenyl Ester Using the representative procedure for N9-alkylation above 4-[3-(6-amino-9H-purin-2-yl)-prop-2-ynyl]-piperidine-1-carboxylic acid 2-chloro-phenyl ester (68 mg) gave the title compound as a white solid: yield 46 mg, 62%. $^1$H NMR (CD$_3$OD) δ 8.21 (s, 1H), 7.41-7.46, 7.34-7.27, 7.24-7.17 (3×m, 4H), 5.03 (d, 2H, J=2.5 Hz), 4.38, 4.18 (2×m, 2H), 3.11, 2.94 (2×m, 2H), 2.98 (t, 1H, J=2.6 Hz), 2.48 (d, 2H, J=6.4 Hz), 2.03-1.82, 1.59-1.32 (2×m, 5H). $^{13}$C NMR (CD$_3$OD) δ 157.1, 154.3, 150.4, 148.9, 147.9, 142.5, 131.1, 129.0, 128.4, 128.0, 125.4, 119.3, 86.2, 82.6, 77.6, 75.9, 46.0, 45.6, 36.5, 33.9, 32.6, 32.4, 26.5. LRMS ESI (M+H$^+$) 449.2.

Example 15

4-[3-(6-Amino-9-prop-2-ynyl-9H-purin-2-yl)-prop-2-ynyl]-piperidine-1-carboxylic acid 2-methoxy-phenyl Ester Using the representative procedure for N9-alkylation above 4-[3-(6-amino-9H-purin-2-yl)-prop-2-ynyl]-piperidine-1-carboxylic acid 2-methoxy-phenyl ester (63 mg) gave the title compound as a white solid: yield 49 mg, 71%. $^1$H NMR (CD$_3$OD) δ 8.20 (s, 1H), 7.20-7.12, 7.05-6.98, 6.93-6.85 (3×m, 4H), 5.02 (d, 2H, J=2.6 Hz), 4.34, 4.16 (2×m, 2H), 3.78 (s, 3H), 3.05, 2.90 (2×m, 2H), 2.99 (t, 1H, J=2.6 Hz), 2.48 (d, 2H, J=6.0 Hz), 1.98-1.80, 1.56-1.30 (2×m, 5H). $^{13}$C NMR (CD$_3$OD) δ 157.1, 155.5, 153.1, 150.4, 147.9, 142.5, 141.9, 127.6, 124.1, 121.7, 119.3, 113.6, 86.3, 82.6, 77.6, 75.9, 56.4, 46.0, 45.5, 36.6, 33.9, 32.6, 32.4, 26.6. LRMS ESI (M+H$^+$) 445.2.

Example 16

2-{3-[1-((3,4-Dimethyl)phenoxycarbanoyl)piperidin-4-yl]propyn-1-yl}-9-propargyladenine Using the representative procedure for N9-alkylation above 2-{3-[1-((3,4-dimethyl)phenoxycarbanoyl)piperidin-4-yl]propyn-1-yl}adenine (33 mg) gave the title compound as a white solid: yield 23 mg, 64%. $^1$H NMR (CD$_3$OD) δ 8.21 (s, 1H), 7.08 (d, 1H, J=8.2 Hz), 6.84 (d, 1H, J=2.3 Hz), 6.78 (dd, 1H, J=8.2 Hz, J=2.5 Hz), 5.02 (d, 2H, J=2.6 Hz), 4.42-4.12 (m, 2H), 3.13-2.84 (m, 3H), 2.48 (d, 2H, J=6.5 Hz), 2.23 (s, 3H), 2.22 (s, 3H), 2.02-1.81, 1.52-1.32 (2×m, 5H). $^{13}$C NMR (CD$_3$OD) δ 157.1, 155.8, 150.8, 150.5, 147.9, 142.5, 138.8, 134.7, 131.1, 123.7, 119.9, 119.3, 86.3, 82.6, 77.2, 75.9, 45.5 (×2), 36.5, 33.9, 32.5 (×2), 26.5, 19.8, 19.1. LRMS ESI (M+H$^+$) 443.2.

Example 17

2-{3-[1-((3,4-Difluoro)phenoxycarbanoyl)piperidin-4-yl]propyn-1-yl}-9-propargyladenine Using the representative procedure for N9-alkylation above 2-{3-[1-((3,4-difluoro)phenoxycarbanoyl)piperidin- 4-yl]propyn-1-yl}adenine (32 mg) gave the title compound as a white solid: yield 15 mg, 43%. $^1$H NMR (CD$_3$OD) δ 8.22 (s, 1H), 7.25 (m, 1H), 7.13 (m, 1H), 6.93 (m, 1H), 5.03 (d, 2H, J=2.5 Hz), 4.30, 4.18 (2×m, 2H), 3.06, 2.92 (2×m, 2H), 2.99 (t, 1H, J=2.6 Hz), 2.48 (d, 2H, J=6.3 Hz), 2.00-1.80, 1.53-1.31 (2×m, 5H). Have 13C but fluorine is splitting a lot of peaks. LRMS ESI (M+H$^+$) 451.2.

Example 18

2-{3-[1-((3,4-Dichloro)phenoxycarbanoyl)piperidin-4-yl]propyn-1-yl}-9-propargyladenine

Using the representative procedure for N9-alkylation above 2-{3-[1-((3,4-dichloro)phenoxycarbanoyl)piperidin-4-yl]propyn-1-yl}-9-propargyladenine (37 mg) gave the title compound as a white solid: yield 11 mg, 28%. $^1$H NMR (CD$_3$OD) δ 8.22 (s, 1H), 7.50 (d, 1H, J=8.8 Hz), 7.36 (d, 1H, J=2.6 Hz), 7.08, (dd, 1H, J=2.6 Hz, J=8.8 Hz), 5.03 (d, 2H, J=2.6 Hz), 4.31, 4.19 (2×m, 2H), 3.07, 2.93 (2×m, 2H), 2.99 (t, 1H, J=2.6 Hz), 2.48 (d, 2H, J=6.2 Hz), 2.00-1.81, 1.54-1.33 (2×m, 5H). LRMS ESI (M+H$^+$) 483.1.

Representative compounds of the present invention are shown below in Table 1. These compounds and their stereoisomers and pharmaceutically acceptable salts are included in the present invention.

TABLE 1

| Ex. # | Y | R$^2$ | R$^4$-R$^3$- | —(CH$_2$)$_q$Z |
|---|---|---|---|---|
| 1. | NH | H | =—CH$_2$— | 4-CH$_3$-phenyl |
| 2. | NH | H | =—CH$_2$— | 4-Cl-phenyl |
| 3. | NH | H | =—CH$_2$— | 3-CH$_3$-phenyl |
| 4. | NH | H | =—CH$_2$— | 3-CF$_3$-phenyl |
| 5. | NH | H | tetrahydrofuran-3-yl | 4-CH$_3$-phenyl |
| 6. | NH | H | tetrahydrofuran-3-yl | 4-Cl-phenyl |
| 7. | NH | H | tetrahydrofuran-3-yl | 3-CH$_3$-phenyl |
| 8. | NH | H | tetrahydrofuran-3-yl | 3-CF$_3$-phenyl |
| 9. | NH | H | cyclopentyl | 4-CH$_3$-phenyl |
| 10. | NH | H | cyclopentyl | 4-Cl-phenyl |
| 11. | NH | H | cyclopentyl | 3-CH$_3$-phenyl |
| 12. | NH | H | cyclopentyl | 3-CF$_3$-phenyl |
| 13. | NH | furan-2-yl | =—CH$_2$— | 4-CH$_3$-phenyl |
| 14. | NH | furan-2-yl | =—CH$_2$— | 4-Cl-phenyl |
| 15. | NH | furan-2-yl | =—CH$_2$— | 3-CH$_3$-phenyl |
| 16. | NH | furan-2-yl | =—CH$_2$— | 3-CF$_3$-phenyl |
| 17. | NH | furan-2-yl | tetrahydrofuran-3-yl | 4-CH$_3$-phenyl |
| 18. | NH | furan-2-yl | tetrahydrofuran-3-yl | 4-Cl-phenyl |
| 19. | NH | furan-2-yl | tetrahydrofuran-3-yl | 3-CH$_3$-phenyl |
| 20. | NH | furan-2-yl | tetrahydrofuran-3-yl | 3-CF$_3$-phenyl |
| 21. | NH | furan-2-yl | cyclopentyl | 4-CH$_3$-phenyl |
| 22. | NH | furan-2-yl | cyclopentyl | 4-Cl-phenyl |
| 23. | NH | furan-2-yl | cyclopentyl | 3-CH$_3$-phenyl |
| 24. | NH | furan-2-yl | cyclopentyl | 3-CF$_3$-phenyl |
| 25. | NH | 2-fluoro-phenyl | =—CH$_2$— | 4-CH$_3$-phenyl |
| 26. | NH | 2-fluoro-phenyl | =—CH$_2$— | 4-Cl-phenyl |
| 27. | NH | 2-fluoro-phenyl | =—CH$_2$— | 3-CH$_3$-phenyl |
| 28. | NH | 2-fluoro-phenyl | =—CH$_2$— | 3-CF$_3$-phenyl |
| 29. | NH | 2-fluoro-phenyl | tetrahydrofuran-3-yl | 4-CH$_3$-phenyl |
| 30. | NH | 2-fluoro-phenyl | tetrahydrofuran-3-yl | 4-Cl-phenyl |
| 31. | NH | 2-fluoro-phenyl | tetrahydrofuran-3-yl | 3-CH$_3$-phenyl |
| 32. | NH | 2-fluoro-phenyl | tetrahydrofuran-3-yl | 3-CF$_3$-phenyl |
| 33. | NH | 2-fluoro-phenyl | cyclopentyl | 4-CH$_3$-phenyl |
| 34. | NH | 2-fluoro-phenyl | cyclopentyl | 4-Cl-phenyl |
| 35. | NH | 2-fluoro-phenyl | cyclopentyl | 3-CH$_3$-phenyl |
| 36. | NH | 2-fluoro-phenyl | cyclopentyl | 3-CF$_3$-phenyl |
| 37. | O | H | =—CH$_2$— | 4-CH$_3$-phenyl |
| 38. | O | H | =—CH$_2$— | 4-Cl-phenyl |
| 39. | O | H | =—CH$_2$— | 3-CH$_3$-phenyl |
| 40. | O | H | =—CH$_2$— | 3-CF$_3$-phenyl |
| 41. | O | H | tetrahydrofuran-3-yl | 4-CH$_3$-phenyl |
| 42. | O | H | tetrahydrofuran-3-yl | 4-Cl-phenyl |
| 43. | O | H | tetrahydrofuran-3-yl | 3-CH$_3$-phenyl |
| 44. | O | H | tetrahydrofuran-3-yl | 3-CF$_3$-phenyl |
| 45. | O | H | cyclopentyl | 4-CH$_3$-phenyl |
| 46. | O | H | cyclopentyl | 4-Cl-phenyl |
| 47. | O | H | cyclopentyl | 3-CH$_3$-phenyl |
| 48. | O | H | cyclopentyl | 3-CF$_3$-phenyl |
| 49. | O | furan-2-yl | =—CH$_2$— | 4-CH$_3$-phenyl |
| 50. | O | furan-2-yl | =—CH$_2$— | 4-Cl-phenyl |
| 51. | O | furan-2-yl | =—CH$_2$— | 3-CH$_3$-phenyl |
| 52. | O | furan-2-yl | =—CH$_2$— | 3-CF$_3$-phenyl |
| 53. | O | furan-2-yl | tetrahydrofuran-3-yl | 4-CH$_3$-phenyl |
| 54. | O | furan-2-yl | tetrahydrofuran-3-yl | 4-Cl-phenyl |
| 55. | O | furan-2-yl | tetrahydrofuran-3-yl | 3-CH$_3$-phenyl |
| 56. | O | furan-2-yl | tetrahydrofuran-3-yl | 3-CF$_3$-phenyl |
| 57. | O | furan-2-yl | cyclopentyl | 4-CH$_3$-phenyl |
| 58. | O | furan-2-yl | cyclopentyl | 4-Cl-phenyl |
| 59. | O | furan-2-yl | cyclopentyl | 3-CH$_3$-phenyl |
| 60. | O | furan-2-yl | cyclopentyl | 3-CF$_3$-phenyl |
| 61. | O | 2-fluoro-phenyl | =—CH$_2$— | 4-CH$_3$-phenyl |
| 62. | O | 2-fluoro-phenyl | =—CH$_2$— | 4-Cl-phenyl |
| 63. | O | 2-fluoro-phenyl | =—CH$_2$— | 3-CH$_3$-phenyl |
| 64. | O | 2-fluoro-phenyl | =—CH$_2$— | 3-CF$_3$-phenyl |
| 65. | O | 2-fluoro-phenyl | tetrahydrofuran-3-yl | 4-CH$_3$-phenyl |
| 66. | O | 2-fluoro-phenyl | tetrahydrofuran-3-yl | 4-Cl-phenyl |
| 67. | O | 2-fluoro-phenyl | tetrahydrofuran-3-yl | 3-CH$_3$-phenyl |
| 68. | O | 2-fluoro-phenyl | tetrahydrofuran-3-yl | 3-CF$_3$-phenyl |
| 69. | O | 2-fluoro-phenyl | cyclopentyl | 4-CH$_3$-phenyl |
| 70. | O | 2-fluoro-phenyl | cyclopentyl | 4-Cl-phenyl |
| 71. | O | 2-fluoro-phenyl | cyclopentyl | 3-CH$_3$-phenyl |
| 72. | O | 2-fluoro-phenyl | cyclopentyl | 3-CF$_3$-phenyl |

Numerous modifications and variations of the present invention are possible in light of the above teachings. It is therefore to be understood that within the scope of the appended claims, the invention may be practiced otherwise that as specifically described herein.

What is claimed is:

1. A compound of formula Ia or Ib or stereoisomer or a pharmaceutically acceptable salt thereof:

-continued

Ib

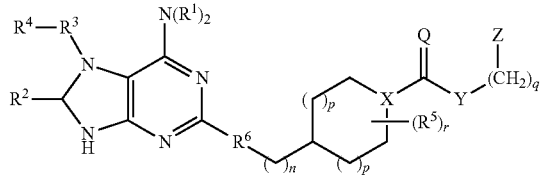

wherein:
the (CH$_2$) portions of (CH$_2$)$_n$ and (CH$_2$)$_q$ are independently substituted with 0-2 groups selected from OH, =O, C$_{1-4}$ alkyl, C$_{3-6}$ cycloalkyl, and benzyl;
Q is O or S;
X is CH or N;
Y is selected from the group consisting of O, NY$^1$, OCH$_2$CH$_2$OCH$_2$, OCH$_2$CH$_2$OCH$_2$CH$_2$OCH$_2$, OCH$_2$CH$_2$OCH$_2$CH$_2$OCH$_2$CH$_2$OCH$_2$, NY$^1$CH$_2$CH$_2$OCH$_2$, NY$^1$CH$_2$CH$_2$OCH$_2$CH$_2$OCH$_2$, and NY$^1$CH$_2$CH$_2$OCH$_2$CH$_2$OCH$_2$CH$_2$OCH$_2$;
alternatively, Y is a bond;
Y$^1$ is selected from the group consisting of H, C$_{1-4}$ alkyl, benzyl, C$_{3-6}$ cycloalkyl, and (C$_{3-6}$ cycloalkyl)C$_{1-4}$ alkylene;
Z is selected from the group consisting of aryl and heteroaryl, wherein Z is attached via a carbon atom and is substituted with 1-4 Z$^1$ groups;
Z$^1$ is independently selected from the group consisting of F, Cl, Br, I, C$_{1-6}$ alkyl, C$_{2-6}$ alkenyl, C$_{2-6}$ alkynyl, —(CH$_2$)$_a$OR$^a$, —(CH$_2$)$_a$NR$^a$R$^a$, —(CH$_2$)$_a$NHOH, —(CH$_2$)$_a$NR$^a$NR$^a$R$^a$, —(CH$_2$)$_a$NO$_2$, —(CH$_2$)$_a$CN, —(CH$_2$)$_a$CO$_2$R$^a$, —(CH$_2$)$_a$C(O)R$^a$, —(CH$_2$)$_a$OC(O)R$^a$, —(CH$_2$)$_a$CONR$^a$R$^a$, CF$_3$, and OCF$_3$;
R$^a$ is independently selected from the group consisting of H, C$_{1-6}$ alkyl, C$_{2-6}$ alkenyl, C$_{2-6}$ alkynyl, C$_{3-8}$ cycloalkyl, (C$_{3-8}$ cycloalkyl)C$_{1-8}$ alkylene, aryl, (aryl)C$_{1-8}$ alkylene, heteroaryl, and (heteroaryl)C$_{1-8}$ alkylene, wherein the alkyl and cycloalkyl optionally are interrupted with 1-2 heteroatoms selected from the group consisting of —O—, —S(O)$_{0-2}$— and —NR$^c$—;
R$^1$ is independently selected from the group consisting of H, C$_{1-8}$ alkyl, C$_{3-8}$ cycloalkyl, (C$_{3-8}$ cycloalkyl)C$_{1-8}$ alkylene, aryl, (aryl)C$_{1-8}$ alkylene, heteroaryl, (heteroaryl)C$_{1-8}$ alkylene, (aryl)(aryl)-C$_{1-8}$ alkylene, (heteroaryl)(heteroaryl)-C$_{1-8}$ alkylene, and (aryl)(heteroaryl)C$_{1-8}$ alkylene, wherein the alkyl and cycloalkyl optionally may be interrupted with 1-2 heteroatoms selected from the group consisting of —O—, —S(O)$_{0-2}$— and —NR$^c$—, and the groups of R$^1$ are substituted with 0-4 groups independently selected from the group consisting of F, Cl, Br, I, C$_{1-6}$ alkyl, C$_{2-6}$ alkenyl, C$_{2-6}$ alkynyl, —(CH$_2$)$_a$OR$^a$, —(CH$_2$)$_a$NR$^a$R$^a$, —(CH$_2$)$_a$NHOH, —(CH$_2$)$_a$NR$^a$NR$^a$R$^a$, —(CH$_2$)$_a$NO$_2$, —(CH$_2$)$_a$CN, —(CH$_2$)$_a$CO$_2$R$^a$, —(CH$_2$)$_a$C(O)R$^a$, —(CH$_2$)$_a$OC(O)R$^a$, —(CH$_2$)$_a$CONR$^a$R$^a$, CF$_3$, and OCF$_3$;
R$^2$ is selected from the group consisting of H, C$_{1-6}$ alkyl, OR$^a$, N(R$^a$)$_2$, C$_{3-8}$ cycloalkyl, aryl, heterocycle, and heteroaryl, wherein the alkyl, cycloalkyl, aryl, heterocycle, and heteroaryl optionally are substituted with 1-2 groups independently selected from the group consisting of F, Cl, I, Br, CH$_3$, CF$_3$, and CH$_3$O;
R$^3$ is a bond or is C$_{1-8}$ alkylene, wherein the alkylene group optionally is interrupted with 1-2 heteroatoms selected from the group consisting of —O—, —S(O)$_{0-2}$— and —NH—;

R$^3$ is unsubstituted or is substituted with 1-2 groups selected from the group consisting of F, Cl, Br, I, —OR$^d$, —SR$^d$, —N(R$^d$)$_2$, C$_{3-6}$ cycloalkyl, (C$_{3-6}$ cycloalkyl)C$_{1-4}$ alkylene, aryl, (aryl)C$_{1-4}$ alkylene, heteroaryl, and (heteroaryl)C$_{1-4}$ alkylene, wherein the alkyl and cycloalkyl optionally are interrupted by 1-2 heteroatoms selected from the group consisting of —O—, —S(O)$_{0-2}$—, and —NR$^c$—;
R$^4$ is selected from the group consisting of C$_{1-8}$ alkyl, C$_{2-8}$ alkenyl, C$_{2-8}$ alkynyl, C$_{3-12}$ cycloalkyl, (C$_{3-12}$ cycloalkyl)C$_{1-8}$ alkylene, aryl, (aryl)C$_{1-8}$ alkylene, heteroaryl, (heteroaryl)C$_{1-8}$ alkylene, CF$_3$, —CO$_2$R$^b$, R$^b$C(O)—, (R$^b$)$_2$NC(O)—, R$^b$OC(S)—, R$^b$C(S)—, and R$^b$S(=O)—, wherein the alkyl and cycloalkyl optionally are interrupted with 1-2 heteroatoms selected from the group consisting of —O—, —S(O)$_{0-2}$— and —NH—, and the alkyl, alkenyl, alkynyl, cycloalkyl, aryl, and heteroaryl are unsubstituted or are substituted with 1-4 groups independently selected from the group consisting of F, Cl, Br, I, C$_{1-6}$ alkyl, C$_{2-6}$ alkenyl, C$_{2-6}$ alkynyl, —(CH$_2$)$_a$OR$^a$, —(CH$_2$)$_a$NR$^a$R$^a$, —(CH$_2$)$_a$NHOH, —(CH$_2$)$_a$NR$^a$NR$^a$R$^a$, —(CH$_2$)$_a$NO$_2$, —(CH$_2$)$_a$CN, —(CH$_2$)$_a$CO$_2$R$^a$, —(CH$_2$)$_a$C(O)R$^a$, —(CH$_2$)$_a$OC(O)R$^a$, —(CH$_2$)$_a$CONR$^a$R$^a$, CF$_3$, OCF$_3$, and —OS(O$_2$)R$^a$;
alternatively, when R$^3$ is present, R$^4$ is additionally selected from the group consisting of H, F, Cl, Br, I, N(R$^b$)$_2$, OR$^b$, SR$^b$, —CN, NO$_2$, CF$_3$O, R$^b$C(O)O—, —OCO$_2$R$^b$, (R$^b$)$_2$NC(O)O—, R$^b$OC(O)NR$^b$—, R$^b$C(O)NR$^b$—, (R$^b$)$_2$NC(O)NR$^b$—, and (R$^b$)$_2$NC(S)NR$^b$—;
provided that when R$^2$ is H and R$^3$ is a bond, then R$^4$ is other than

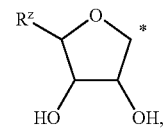

wherein:
(a) "*" is the point of attachment;
(b) R$^z$ is —CH$_2$OR, —CO$_2$R, —OC(O)R, —CH$_2$OC(O)R, —CH$_2$SR, —C(S)OR, —CH$_2$OC(S)R, —CH$_2$NRR, —C(S)NRR, and, —C(O)NRR; and,
(c) R is H or a substituent;
R$^b$ is independently selected from the group consisting of H, C$_{1-6}$ alkyl, C$_{2-6}$ alkenyl, C$_{2-6}$ alkynyl, C$_{3-8}$ cycloalkyl, (C$_{3-8}$ cycloalkyl)C$_{1-8}$ alkylene, aryl, (aryl)C$_{1-8}$ alkylene, heteroaryl, and (heteroaryl)C$_{1-8}$ alkylene, wherein the alkyl and cycloalkyl optionally are interrupted with 1-2 heteroatoms selected from the group consisting of —O—, —S(O)$_{0-2}$— and —NH— and wherein the alkyl, cycloalkyl, aryl, and heteroaryl are substituted with 0-4 substituents selected from the group consisting of F, Cl, Br, I, C$_{1-6}$ alkyl, C$_{2-6}$ alkenyl, C$_{2-6}$ alkynyl, —(CH$_2$)$_a$OR$^a$, —(CH$_2$)$_a$NR$^a$R$^a$, —(CH$_2$)$_a$NHOH, —(CH$_2$)$_a$NR$^a$NR$^a$R$^a$, —(CH$_2$)$_a$NO$_2$, —(CH$_2$)$_a$CN, —(CH$_2$)$_a$CO$_2$R$^a$, —(CH$_2$)$_a$C(O)R$^a$, —(CH$_2$)$_a$OC(O)R$^a$, —(CH$_2$)$_a$CONR$^a$R$^a$, CF$_3$, and OCF$_3$;
R$^c$ is independently selected from the group consisting of H, C$_{1-6}$ alkyl, and benzyl;
R$^d$ is independently selected from the group consisting of H, C$_{1-6}$ alkyl, C$_{3-6}$ cycloalkyl, (C$_{3-6}$ cycloalkyl)C$_{1-4}$ alkylene, phenyl, and benzyl;
R$^5$ is independently selected from the group consisting of H, F, Cl, Br, I, —OR$^c$, —N(R$^c$)$_2$, C$_{1-6}$ alkyl, C$_{3-6}$ cycloalkyl, aryl, and (aryl)C$_{1-4}$ alkylene, wherein the alkyl and cycloalkyl optionally are interrupted by 1-2 heteroatoms selected from the group consisting of —O—, —S(O)$_{0-2}$—, and —NR$^b$—;

R$^6$ is selected from the group consisting of CH$_2$CH$_2$, CH=CH, and C≡C;

a is independently selected from the group consisting of 0, 1, and 2;

n is independently selected from the group consisting of 0, 1, and 2;

p is independently selected from the group consisting of 0, 1, and 2;

q is independently selected from the group consisting of 0, 1, and 2; and, r is independently selected from the group consisting of 0, 1, and 2.

2. The compound according to claim 1, wherein the compound is of formula IIa or IIIa:

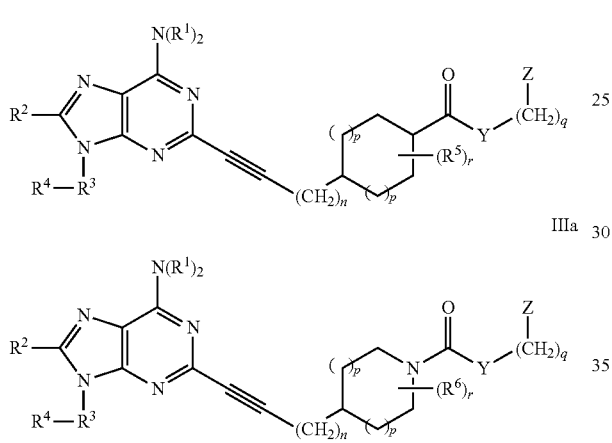

wherein:

Y is selected from the group consisting of O, NY$^1$, OCH$_2$CH$_2$OCH$_2$, and, NY$^1$CH$_2$CH$_2$OCH$_2$;

alternatively, Y is a bond;

Y$^1$ is selected from the group consisting of H and CH$_3$;

Z is selected from the group consisting of 5-6 membered heteroaryl and phenyl, wherein Z is attached via a carbon atom and is substituted with 1-4 Z$^1$ groups;

Z$^1$ is independently selected from the group consisting of F, Cl, C$_{1-4}$ alkyl, C$_{2-4}$ alkenyl, C$_{2-4}$ alkynyl, —(CH$_2$)$_a$OR$^a$, —(CH$_2$)$_a$NR$^a$R$^a$, —(CH$_2$)$_a$NHOH, —(CH$_2$)$_a$NR$^a$NR$^a$R$^a$, —(CH$_2$)$_a$NO$_2$, —(CH$_2$)$_a$CN, —(CH$_2$)$_a$CO$_2$R$^a$, —(CH$_2$)$_a$C(O)R$^a$, —(CH$_2$)$_a$OC(O)R$^a$, —(CH$_2$)$_a$CONR$^a$R$^a$, CF$_3$, and OCF$_3$;

R$^a$ is independently selected from the group consisting of H, C$_{1-4}$ alkyl, C$_{2-4}$ alkenyl, C$_{2-4}$ alkynyl, C$_{3-6}$ cycloalkyl, (C$_{3-6}$ cycloalkyl)C$_{1-2}$ alkylene, aryl, (aryl)C$_{1-2}$ alkylene, heteroaryl, and (heteroaryl)C$_{1-2}$ alkylene, wherein the alkyl and cycloalkyl optionally are interrupted with 1-2 heteroatoms selected from the group consisting of —O—, —S(O)$_{0-2}$— and —NR$^c$—;

R$^1$ is independently selected from the group consisting of H, C$_{1-4}$ alkyl, C$_{3-6}$ cycloalkyl, (C$_{3-6}$ cycloalkyl)C$_{1-4}$ alkylene, aryl, (aryl)C$_{1-4}$ alkylene, heteroaryl, (heteroaryl)C$_{1-4}$ alkylene, (aryl)(aryl)-C$_{1-4}$ alkylene, (heteroaryl)(heteroaryl)-C$_{1-4}$ alkylene, and (aryl)(heteroaryl)C$_{1-2}$ alkylene, wherein the alkyl and cycloalkyl optionally are interrupted with 1-2 heteroatoms selected from the group consisting of —O—, —S(O)$_{0-2}$— and —NR$^c$— and the aryl and heteroaryl rings are substituted with 0-2 groups independently selected from the group consisting of F, Cl, C$_{1-4}$ alkyl, C$_{2-4}$ alkenyl, C$_{2-4}$ alkynyl, —(CH$_2$)$_a$OR$^a$, —(CH$_2$)$_a$NR$^a$R$^a$, —(CH$_2$)$_a$NHOH, —(CH$_2$)$_a$NR$^a$NR$^a$R$^a$, —(CH$_2$)$_a$NO$_2$, —(CH$_2$)$_a$CN, —(CH$_2$)$_a$CO$_2$R$^a$, —(CH$_2$)$_a$C(O)R$^a$, —(CH$_2$)$_a$OC(O)R$^a$, —(CH$_2$)$_a$CONR$^a$R$^a$, CF$_3$, and OCF$_3$;

R$^2$ is selected from the group consisting of H, C$_{1-4}$ alkyl, OR$^a$, N(R$^a$)$_2$, C$_{3-6}$ cycloalkyl, aryl, heterocycle, and heteroaryl, wherein the alkyl, cycloalkyl, aryl, heterocycle, and heteroaryl are substituted with 0-2 groups independently selected from the group consisting of F, Cl, CH$_3$, CF$_3$, and CH$_3$O;

R$^4$ is selected from the group consisting of C$_{1-4}$ alkyl, C$_{2-4}$ alkenyl, C$_{2-4}$ alkynyl, C$_{3-6}$ cycloalkyl, (C$_{3-6}$ cycloalkyl)C$_{1-2}$ alkylene, aryl, (aryl)C$_{1-2}$ alkylene, heteroaryl, (heteroaryl)C$_{1-2}$ alkylene, CF$_3$, —CO$_2$R$^b$, R$^b$C(O)—, (R$^b$)$_2$NC(O)—, R$^b$OC(S)—, R$^b$C(S)—, and R$^b$S(=O)—, wherein the alkyl and cycloalkyl optionally are interrupted with 1-2 heteroatoms selected from the group consisting of —O—, —S(O)$_{0-2}$— and —NH—, and the alkyl, alkenyl, alkynyl, cycloalkyl, aryl, and heteroaryl are substituted with 0-3 groups independently selected from the group consisting of F, Cl, C$_{1-4}$ alkyl, C$_{2-4}$ alkenyl, C$_{2-4}$ alkynyl, —(CH$_2$)$_a$OR$^a$, —(CH$_2$)$_a$NR$^a$R$^a$, —(CH$_2$)$_a$NHOH, —(CH$_2$)$_a$NR$^a$NR$^a$R$^a$, —(CH$_2$)$_a$NO$_2$, —(CH$_2$)$_a$CN, —(CH$_2$)$_a$CO$_2$R$^a$, —(CH$_2$)$_a$C(O)R$^a$, —(CH$_2$)$_a$OC(O)R$^a$, —(CH$_2$)$_a$CONR$^a$R$^a$, CF$_3$, OCF$_3$, and —OS(O$_2$)R$^a$;

alternatively, when R$^3$ is at least 1, R$^4$ additionally may be selected from the group consisting of H, F, Cl, N(R$^b$)$_2$, OR$^b$, SR$^b$, —CN, NO$_2$, CF$_3$O, R$^b$C(O)O—, —OCO$_2$R$^b$, (R$^b$)$_2$NC(O)O—, R$^b$OC(O)NR$^b$—, R$^b$C(O)NR$^b$—, (R$^b$)$_2$NC(O)NR$^b$—, and (R$^b$)$_2$NC(S)NR$^b$—;

provided that when R$^2$ is H and R$^3$ is a bond, then R$^4$ is other than

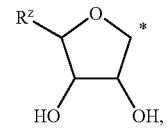

wherein:

(a) "*" is the point of attachment;

(b) R$^z$ is —CH$_2$OR, —CO$_2$R, —OC(O)R, —CH$_2$OC(O)R, —CH$_2$SR, —C(S)OR, —CH$_2$OC(S)R, —CH$_2$NRR, —C(S)NRR, and, —C(O)NRR; and, (c) R is H or a substituent;

R$^b$ is independently selected from the group consisting of H, C$_{1-4}$ alkyl, C$_{2-4}$ alkenyl, C$_{2-4}$ alkynyl, C$_{3-6}$ cycloalkyl, (C$_{3-6}$ cycloalkyl)C$_{1-2}$ alkylene, aryl, (aryl)C$_{1-2}$ alkylene, heteroaryl, and (heteroaryl)C$_{1-2}$ alkylene, wherein the alkyl and cycloalkyl optionally are interrupted with 1-2 heteroatoms selected from the group consisting of —O—, —S(O)$_{0-2}$— and —NH— and wherein the alkyl, cycloalkyl, aryl, and heteroaryl are substituted with 0-2 substituents selected from the group consisting of F, Cl, C$_{1-4}$ alkyl, C$_{2-4}$ alkenyl, C$_{2-4}$ alkynyl, —(CH$_2$)$_a$OR$^a$, —(CH$_2$)$_a$NR$^a$R$^a$, —(CH$_2$)$_a$NHOH, —(CH$_2$)$_a$NR$^a$NR$^a$R$^a$, —(CH$_2$)$_a$NO$_2$, —(CH$_2$)$_a$CN, —(CH$_2$)$_a$CO$_2$R$^a$, —(CH$_2$)$_a$C(O)R$^a$, —(CH$_2$)$_a$OC(O)R$^a$, —(CH$_2$)$_a$CONR$^a$R$^a$, CF$_3$, and OCF$_3$;

R³ is a bond or is C₁₋₄ alkylene, wherein the alkylene group optionally is interrupted with a heteroatom selected from the group consisting of —O—, —S(O)₀₋₂— and —NH—;

R³ is substituted with 0-1 groups selected from the group consisting of F, Cl, —OR$^d$, —SR$^d$, —N(R$^d$)₂, C₃₋₆ cycloalkyl, (C₃₋₆ cycloalkyl)C₁₋₂ alkylene, aryl, (aryl)C₁₋₂ alkylene, heteroaryl, and (heteroaryl)C₁₋₂ alkylene, wherein the alkyl and cycloalkyl optionally are interrupted by 1-2 heteroatoms selected from the group consisting of —O—, —S(O)₀₋₂—, and —NR$^c$—;

R$^c$ is independently selected from the group consisting of H and C₁₋₄ alkyl;

R$^d$ is independently selected from the group consisting of H, C₁₋₄ alkyl, (C₃₋₆ cycloalkyl)C₁₋₂ alkylene, and benzyl;

R⁵ is independently selected from the group consisting of H, F, Cl, —N(R$^c$)₂, C₁₋₄ alkyl, C₃₋₆ cycloalkyl, aryl, and (aryl)C₁₋₂ alkylene, wherein the alkyl and cycloalkyl optionally are interrupted by 1 heteroatom selected from the group consisting of —O—, —S(O)₀₋₂—, and —NR$^b$—;

a is independently selected from the group consisting of 0 and 1;

n is independently selected from the group consisting of 0 and 1;

p is independently selected from the group consisting of 0 and 1;

q is independently selected from the group consisting of 0 and 1; and, r is independently selected from the group consisting of 0 and 1.

3. The compound according to claim 2, wherein:

Y is selected from the group consisting of O and OCH₂CH₂OCH₂;

alternatively, Y is a bond;

Z is selected from the group consisting of phenyl, pyridyl, and pyrimidyl, wherein Z is attached via a carbon atom and is substituted with 1-3 Z¹ groups;

Z¹ is independently selected from the group consisting of F, Cl, C₁₋₄ alkyl, C₂₋₄ alkenyl, C₂₋₄ alkynyl, OR$^a$, NHOH, NR$^a$NR$^a$R$^a$, NO₂, CO₂R$^a$, C(O)R$^a$, OC(O)R$^a$, CONR$^a$R$^a$, CF₃, and OCF₃;

R¹ is independently selected from the group consisting of H, C₁₋₄ alkyl, (cyclopropyl)CH₂—, benzyl, pyridyl-CH₂—, (phenyl)(phenyl)-C₁₋₄ alkylene, (pyridyl)(pyridyl)-C₁₋₄ alkylene, and (phenyl)(pyridyl)C₁₋₄ alkylene, wherein the aryl and heteroaryl rings are substituted with 0-2 groups independently selected from the group consisting of F, Cl, CH₃, OH, OCH₃, NH₂, NHCH₃, N(CH₃)₂, NHOH, NHNH₂, NO₂, CN, CO₂CH₃, C(O)CH₃, CONH₂, C(O)NHCH₃, C(O)N(CH₃)₂, CF₃, and OCF₃;

R² is selected from the group consisting of H, OR$^a$, N(R$^a$)₂, phenyl, and 5-6 membered heteroaryl, wherein the aryl and heteroaryl are substituted with 0-2 groups independently selected from the group consisting of F, Cl, CH₃, CF₃, and CH₃O;

R³ is a bond or is C₁₋₂ alkylene;

R⁴ is selected from the group consisting of C₂₋₄ alkenyl, C₂₋₄ alkynyl, cyclopropyl, cyclobutyl, cyclopentyl, cyclohexyl, phenyl, naphthyl, heteroaryl, wherein the cycloalkyls optionally are interrupted with a heteroatom selected from the group consisting of —O—, —S(O)₀₋₂— and —NH—, and the alkenyl, alkynyl, cycloalkyl, aryl, and heteroaryl are substituted with 0-2 groups independently selected from the group consisting of F, Cl, CH₃, OH, OCH₃, NH₂, NHCH₃, N(CH₃)₂, NHOH, NHNH₂, NO₂, CN, CO₂CH₃, C(O)CH₃, CONH₂, C(O)NHCH₃, C(O)N(CH₃)₂, CF₃, and OCF₃;

R⁵ is independently selected from the group consisting of H and CH₃;

n is 1;

p is 1;

q is independently selected from the group consisting of 0 and 1; and, r is independently selected from the group consisting of 0 and 1.

4. The compound according to claim 3, wherein:

Z is selected from the group consisting of phenyl, pyridyl, and pyrimidyl, wherein Z is attached via a carbon atom and is substituted with 1 Z¹ group: and, Z¹ is independently selected from the group consisting of F, Cl, CH₃, CH₂CH₃, OH, OCH₃, NH₂, NHCH₃, N(CH₃)₂, NHOH, NHNH₂, NO₂, CN, CO₂CH₃, C(O)CH₃, CONH₂, C(O)NHCH₃, C(O)N(CH₃)₂, CF₃, and OCF₃.

5. The compound according to claim 2, wherein the compound is of formula IIa.

6. The compound according to claim 5, wherein p is 1.

7. The compound according to claim 6, wherein r is 0.

8. The compound according to claim 7, wherein Y is O.

9. The compound according to claim 8, wherein the compound is of formula IIb:

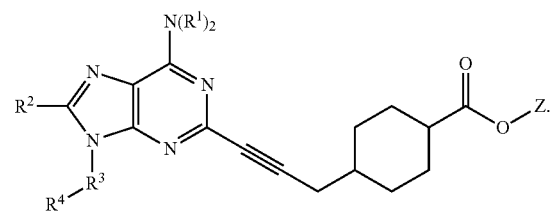

IIb

10. The compound according to claim 2, wherein the compound is of formula IIIa.

11. The compound according to claim 10, wherein p is 1.

12. The compound according to claim 11 wherein r is 0.

13. The compound according to claim 12, wherein Y is O.

14. The compound according to claim 13, wherein the compound is of formula IIIb:

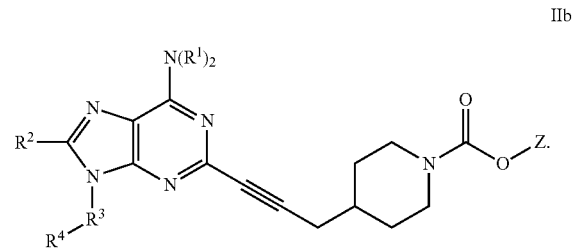

IIb

15. A compound selected from:

4-[3-(6-Amino-9-prop-2-ynyl-9H-purin-2-yl)-prop-2-ynyl]-piperidine-1-carboxylic acid 2-benzyloxy-ethyl ester;

4-[3-(6-Amino-9-cyclopentyl-9H-purin-2-yl)-prop-2-ynyl]-piperidine-1-carboxylic acid 2-benzyloxy-ethyl ester;
4-[3-(6-Amino-9-prop-2-ynyl-9H-purin-2-yl)-prop-2-ynyl]-piperidine-1-carboxylic acid 3-trifluoromethyl-phenyl ester;
4-[3-(6-Amino-9-cyclopentyl-9H-purin-2-yl)-prop-2-ynyl]-piperidine-1-carboxylic acid 3-trifluoromethyl-phenyl ester;
4-[3-(6-Amino-9-prop-2-ynyl-9H-purin-2-yl)-prop-2-ynyl]-piperidine-1-carboxylic acid 2-fluoro-phenyl ester;
4-[3-(6-Amino-9-prop-2-ynyl-9H-purin-2-yl)-prop-2-ynyl]-piperidine-1-carboxylic acid 4-nitro-phenyl ester;
4-[3-(6-Amino-9-prop-2-ynyl-9H-purin-2-yl)-prop-2-ynyl]-piperidine-1-carboxylic acid 4-methoxycarbonyl-phenyl ester;
4-[3-(6-Amino-9-prop-2-ynyl-9H-purin-2-yl)-prop-2-ynyl]-piperidine-1-carboxylic acid 4-chloro-phenyl ester;
4-[3-(6-Amino-9-prop-2-ynyl-9H-purin-2-yl)-prop-2-ynyl]-piperidine-1-carboxylic acid 4-methoxy-phenyl ester;
4-[3-(6-Amino-9-prop-2-ynyl-9H-purin-2-yl)-prop-2-ynyl]-piperidine-1-carboxylic acid 4-methyl-phenyl ester;
4-[3-(6-Amino-9-prop-2-ynyl-9H-purin-2-yl)-prop-2-ynyl]-piperidine-1-carboxylic acid 4-nitro-benzyl ester;
4-[3-(6-Amino-9-prop-2-ynyl-9H-purin-2-yl)-prop-2-ynyl]-piperidine-1-carboxylic acid 2-chloro-phenyl ester;
4-[3-(6-Amino-9-prop-2-ynyl-9H-purin-2-yl)-prop-2-ynyl]-piperidine-1-carboxylic acid 2-methoxy-phenyl ester;
2-{3-[1-((3,4-Dimethyl)phenoxycarbonyl)piperidin-4-yl]propyn-1-yl}-9-propargyladenine;
2-{3-[1-((3,4-Difluoro)phenoxycarbonyl)piperidin-4-yl]propyn-1-yl}-9-propargyladenine; and,
2-{3-[1-((3,4-Dichloro)phenoxycarbonyl)piperidin-4-yl]propyn-1-yl}-9-propargyladenine.

16. A compound selected from a compound of Table A:

TABLE A

| Ex. No. | R | X | $R^9$ |
|---|---|---|---|
| 1 | Phenyl | O | Propargyl |
| 2 | Phenyl | O | Cyclopentyl |
| 3 | —CH$_2$CH$_2$OBn | O | Propargyl |
| 4 | —CH$_2$CH$_2$OBn | O | Cyclopentyl |
| 5 | 3-Trifluoromethylphenyl | O | Propargyl |
| 6 | 3-Trifluoromethylphenyl | O | Cyclopentyl |
| 7 | 4-Fluorophenyl | O | Propargyl |
| 8 | 4-Nitrophenyl | O | Propargyl |
| 9 | 4-(methoxycarbonyl)phenyl | O | Propargyl |
| 10 | 4-Chlorophenyl | O | Propargyl |
| 11 | 4-Methoxyphenyl | O | Propargyl |
| 12 | 4-Methylphenyl | O | Propargyl |
| 13 | 4-Nitrobenzyl | O | Propargyl |
| 14 | 2-Chlorophenyl | O | Propargyl |
| 15 | 2-Methoxyphenyl | O | Propargyl |
| 16 | 3,4-Dimethylphenyl | O | Propargyl |
| 17 | 3,4-Difluorophenyl | O | Propargyl |
| 18 | 3,4-Dichlorophenyl | O | Propargyl. |

17. A pharmaceutical composition comprising: a therapeutically effective amount of a compound of claim 1 and a pharmaceutically acceptable carrier.

18. A pharmaceutical composition comprising: a therapeutically effective amount of a compound of claim 15 and a pharmaceutically acceptable carrier.

19. A pharmaceutical composition comprising: a therapeutically effective amount of a compound of claim 16 and a pharmaceutically acceptable carrier.

* * * * *